(12) United States Patent
Rogers et al.

(10) Patent No.: US 11,452,614 B2
(45) Date of Patent: *Sep. 27, 2022

(54) EXPANDABLE AND ADJUSTABLE LORDOSIS INTERBODY FUSION SYSTEM

(71) Applicant: Adcura, Inc., Eden Prairie, MN (US)

(72) Inventors: Andrew Rogers, Deephaven, MN (US); Robyn Burrows-Ownbey, Elmdale, KS (US)

(73) Assignee: Adcura, Inc., Eden Prairie, MN (US)

( * ) Notice: Subject to any disclaimer, the term of this patent is extended or adjusted under 35 U.S.C. 154(b) by 383 days.

This patent is subject to a terminal disclaimer.

(21) Appl. No.: 16/569,621

(22) Filed: Sep. 12, 2019

(65) Prior Publication Data

US 2020/0078190 A1    Mar. 12, 2020

Related U.S. Application Data

(63) Continuation-in-part of application No. 16/001,852, filed on Jun. 6, 2018, now Pat. No. 10,758,369, which
(Continued)

(51) Int. Cl.
- *A61F 2/44* (2006.01)
- *A61F 2/46* (2006.01)
- *A61F 2/30* (2006.01)

(52) U.S. Cl.
CPC ............ *A61F 2/447* (2013.01); *A61F 2/4455* (2013.01); *A61F 2/4611* (2013.01); *A61F 2/4465* (2013.01);
(Continued)

(58) Field of Classification Search
CPC ........ A61F 2/447; A61F 2/4455; A61F 2/446; A61F 2/4465
See application file for complete search history.

(56) References Cited

U.S. PATENT DOCUMENTS

| | | |
|---|---|---|
| 5,171,278 A | 12/1992 | Pisharodi |
| 5,653,763 A | 8/1997 | Errico |

(Continued)

FOREIGN PATENT DOCUMENTS

| | | |
|---|---|---|
| CN | 201861800 | 6/2011 |
| CN | 102369332 | 3/2012 |

(Continued)

OTHER PUBLICATIONS

Japanese Patent Office, Office Action in Japanese Application No. 2016-537917, dated Jun. 4, 2018, 9 pages.
(Continued)

*Primary Examiner* — Amy R Sipp
(74) *Attorney, Agent, or Firm* — Adcura IP

(57) ABSTRACT

A spinal implant device for placement between vertebral bodies includes a housing, at least one screw member in the housing, and at least one drive shaft operably engageable with the screw member. The housing includes a first shell member and a second shell member. At least the first shell member has step tracking comprising a plurality of individual riser members for receiving the at least one screw member. The height of the plurality of individual riser members may change along the step tracking. The drive shaft may be operable to rotate the at least one screw member, causing the at least one screw member to move on the plurality of individual riser members. The at least one screw member comprises an external helical thread having a thickness configured to fit in the gaps between adjacent individual riser members, and is engageable with the first and second shell members, whereby the first and second shell members move relative to each other in response to the rotation of the at least one screw member to effect an expansion of the housing or a contraction of the housing
(Continued)

from the expansion by reversing the rotation of the at least one screw member.

21 Claims, 30 Drawing Sheets

Related U.S. Application Data is a continuation of application No. 15/859,241, filed on Dec. 29, 2017, now Pat. No. 10,188,527, which is a continuation of application No. 14/473,200, filed on Aug. 29, 2014, now Pat. No. 9,889,019.

(60) Provisional application No. 62/736,649, filed on Sep. 26, 2018, provisional application No. 61/871,780, filed on Aug. 29, 2013.

(52) U.S. Cl.
CPC ............ *A61F 2002/30462* (2013.01); *A61F 2002/30507* (2013.01); *A61F 2002/30523* (2013.01); *A61F 2002/30525* (2013.01); *A61F 2002/30538* (2013.01); *A61F 2002/30556* (2013.01); *A61F 2002/30566* (2013.01); *A61F 2002/4627* (2013.01)

(56) References Cited

U.S. PATENT DOCUMENTS

| | | | |
|---|---|---|---|
| 5,665,122 A | 9/1997 | Kambin | |
| 5,693,100 A | 12/1997 | Pisharodi | |
| 6,129,763 A | 10/2000 | Chauvin | |
| 6,159,244 A | 12/2000 | Suddaby | |
| 6,174,334 B1 | 1/2001 | Suddaby | |
| 6,193,757 B1 | 2/2001 | Foley | |
| 6,436,140 B1 | 8/2002 | Liu | |
| 6,641,614 B1* | 11/2003 | Wagner | A61F 2/4455 623/17.15 |
| 6,905,512 B2 | 6/2005 | Paes | |
| 7,094,257 B2 | 8/2006 | Mujwid | |
| 7,431,735 B2* | 10/2008 | Liu | A61F 2/4611 623/17.11 |
| 7,569,074 B2 | 8/2009 | Eisermann | |
| 7,674,296 B2 | 3/2010 | Rhoda | |
| 7,708,778 B2 | 5/2010 | Gordon | |
| 7,753,958 B2 | 7/2010 | Gordon | |
| D626,233 S | 10/2010 | Cipoletti | |
| 8,062,375 B2 | 11/2011 | Glerum | |
| 8,192,495 B2 | 6/2012 | Simpson | |
| 8,221,501 B2 | 7/2012 | Eisermann | |
| 8,303,663 B2 | 11/2012 | Jimenez | |
| 8,394,143 B2 | 3/2013 | Grotz | |
| 8,398,713 B2 | 3/2013 | Weiman | |
| 2002/0151977 A1 | 10/2002 | Paes | |
| 2002/0161444 A1 | 10/2002 | Choi | |
| 2003/0128902 A1* | 7/2003 | Kennedy | F16C 43/02 384/275 |
| 2004/0153156 A1* | 8/2004 | Cohen | A61F 2/44 623/17.13 |
| 2005/0010295 A1 | 1/2005 | Michelson | |
| 2005/0065605 A1 | 3/2005 | Jackson | |
| 2005/0283244 A1 | 12/2005 | Gordon | |
| 2005/0283245 A1 | 12/2005 | Gordon | |
| 2006/0129244 A1 | 6/2006 | Ensign | |
| 2006/0149385 A1 | 7/2006 | McKay | |
| 2006/0206207 A1 | 9/2006 | Dryer | |
| 2006/0241770 A1 | 10/2006 | Rhoda | |
| 2007/0053765 A1* | 3/2007 | Warnick | A61B 17/863 411/378 |
| 2008/0147194 A1 | 6/2008 | Grotz | |
| 2008/0300598 A1 | 12/2008 | Barreiro | |
| 2009/0210062 A1 | 8/2009 | Thalgott | |
| 2009/0222100 A1 | 9/2009 | Cipoletti | |
| 2010/0082109 A1 | 4/2010 | Greenhalgh | |
| 2010/0185291 A1 | 7/2010 | Jimenez | |
| 2011/0035011 A1 | 2/2011 | Cain | |
| 2012/0290097 A1 | 11/2012 | Cipoletti | |
| 2012/0323327 A1 | 12/2012 | McAfee | |
| 2013/0053966 A1 | 2/2013 | Jimenez | |
| 2013/0173003 A1 | 7/2013 | Matthis et al. | |
| 2013/0211526 A1 | 8/2013 | Alheidt | |
| 2018/0116818 A1 | 5/2018 | Rogers et al. | |

FOREIGN PATENT DOCUMENTS

| | | |
|---|---|---|
| EP | 1925272 | 1/2010 |
| EP | 1706075 | 1/2011 |
| EP | 1903994 | 6/2011 |
| WO | 2005058209 | 6/2005 |
| WO | 2009124269 | 10/2009 |
| WO | 2012112596 | 8/2012 |

OTHER PUBLICATIONS

PCT, International Search Report and Written Opinion of International Searching Authority in PCT/US2014/53551, dated Dec. 18, 2014, 12 pages.

EPO, Office Action and Written Opinion EP 14841270.3, dated Apr. 20, 2017, 5 pages.

PCT, International Search Report and Written Opinion of the International Searching Authority in PCT/US19/50904, dated Dec. 5, 2019, 10 pages.

Billllongsoftware, "Jun. 2016 Final Sagittae Video," URL=http://www.youtube.com/watch?v=BqplG6C1R4A, Sep. 12, 2018, 3 pages.

\* cited by examiner

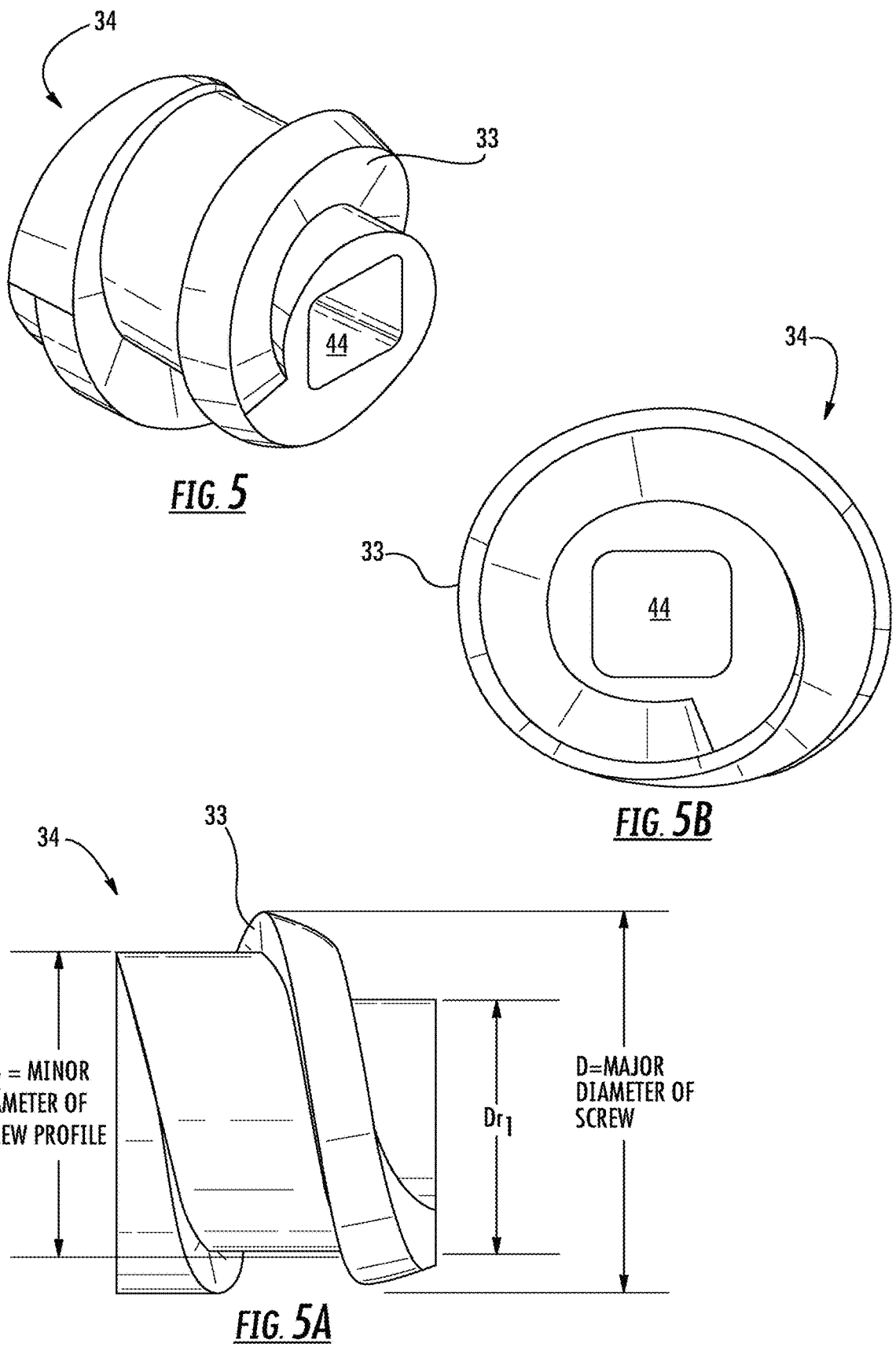

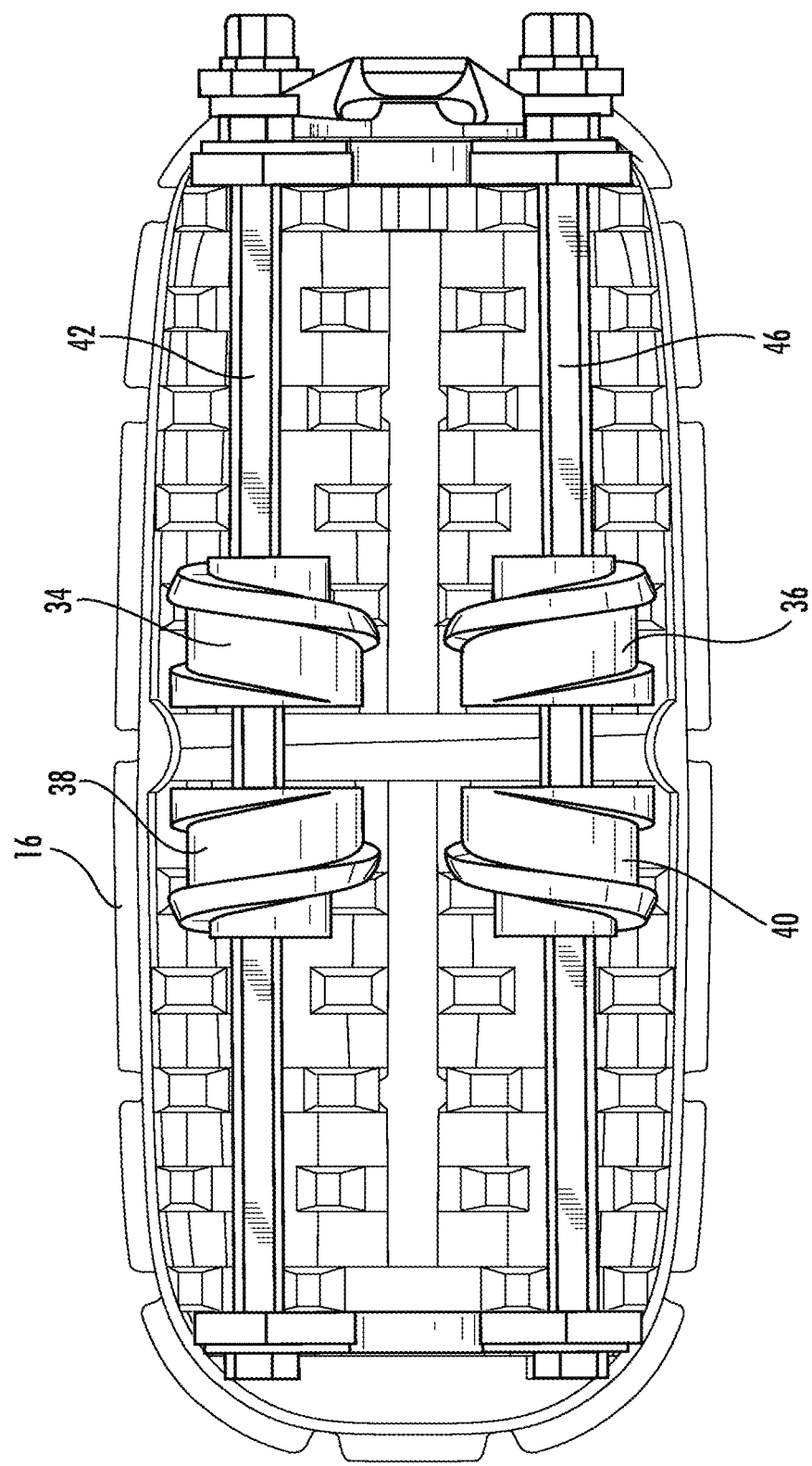

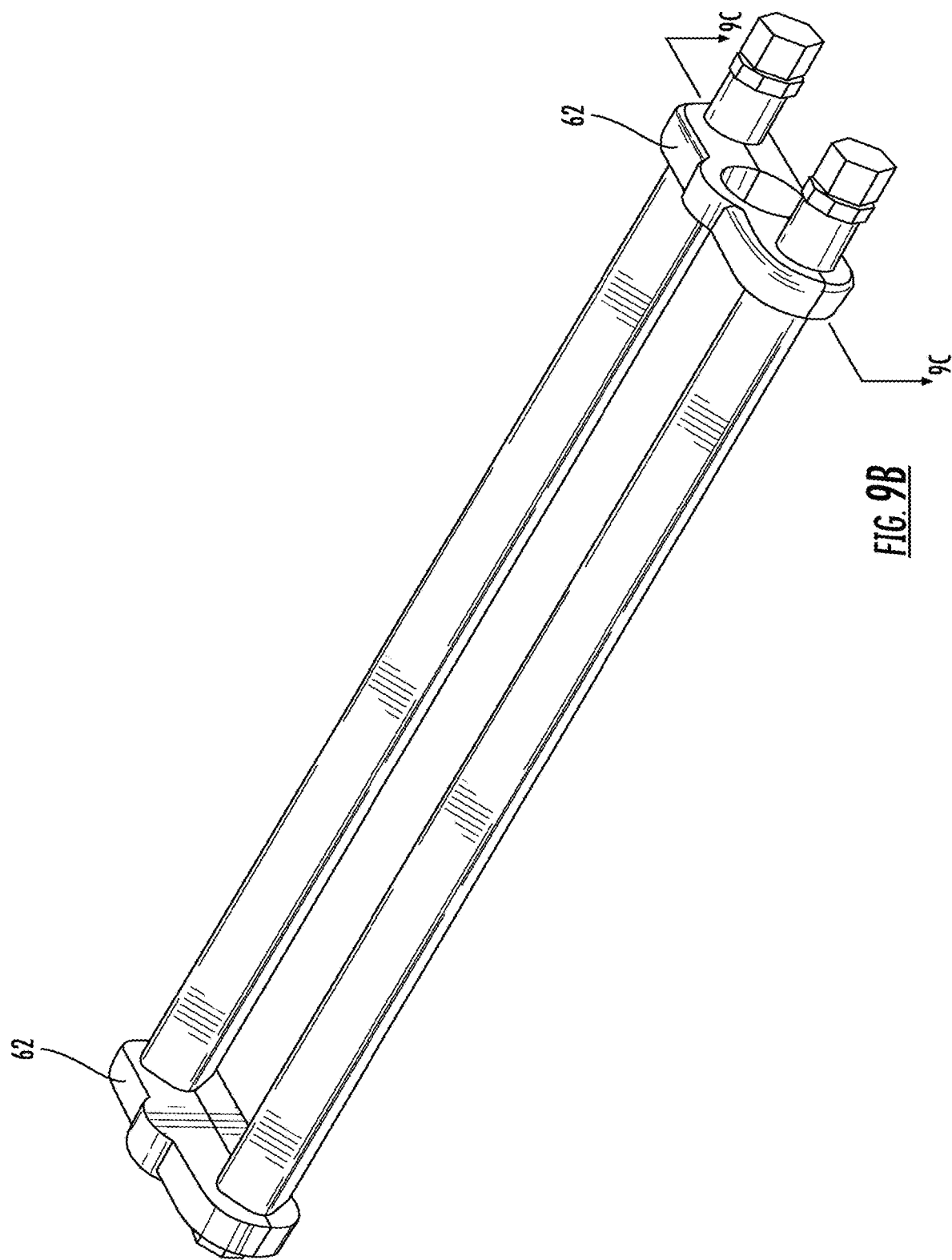

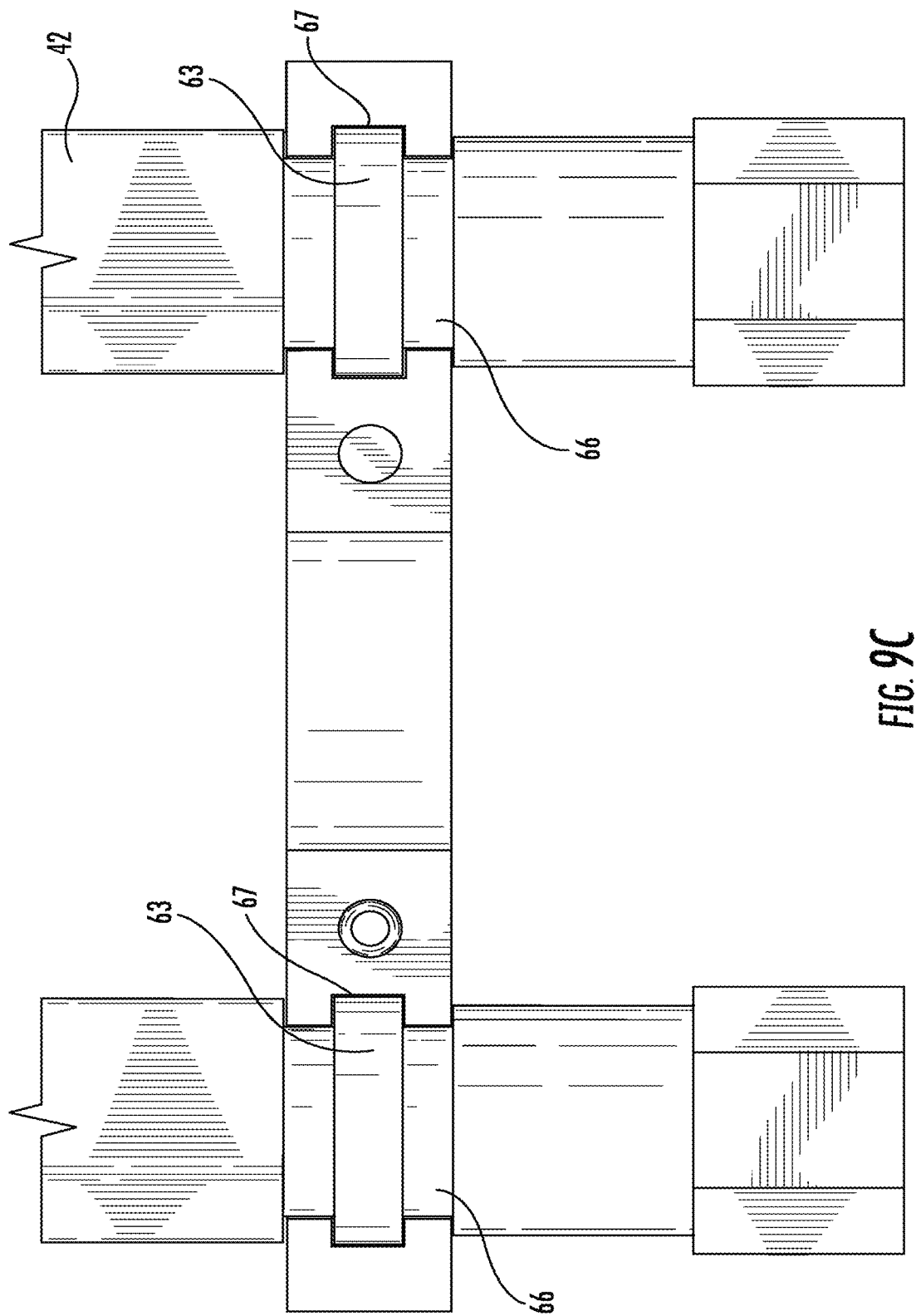

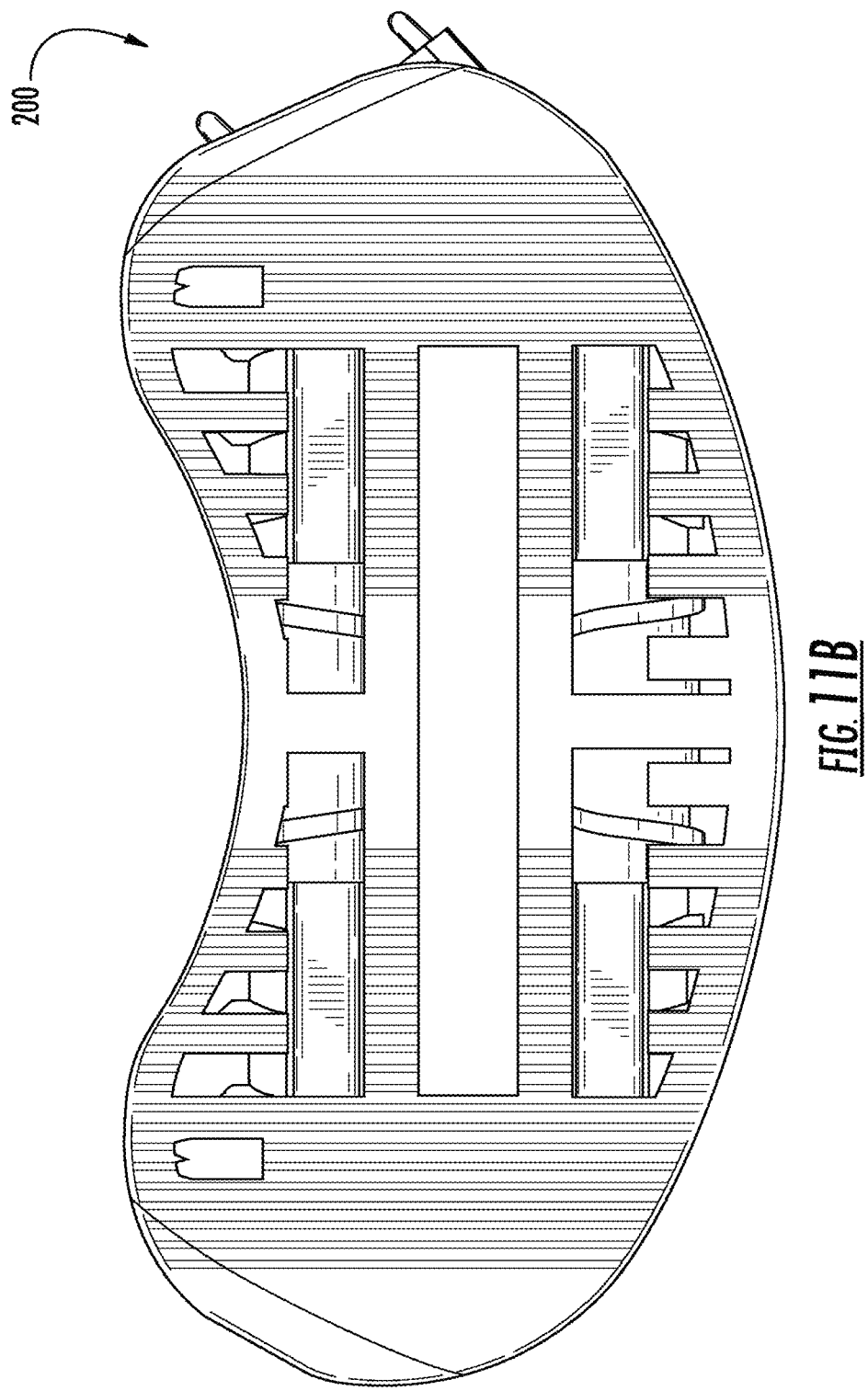

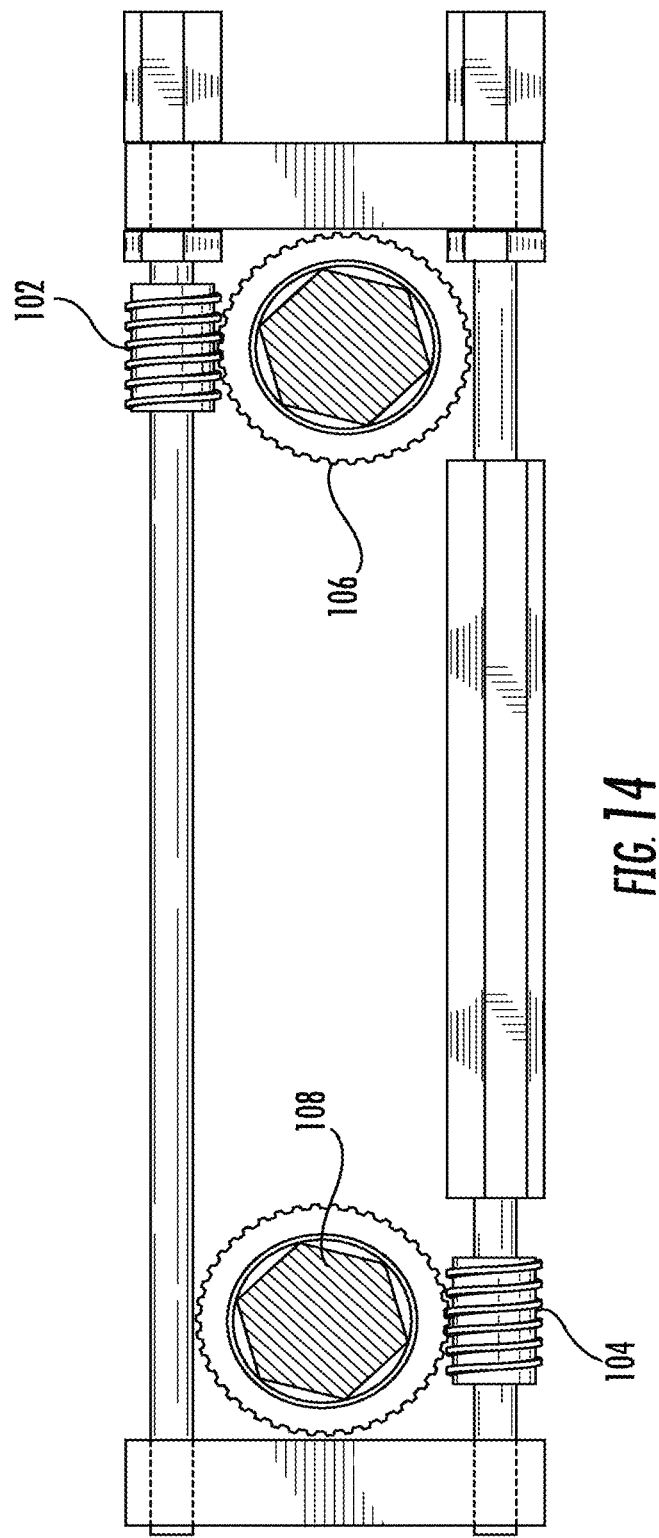

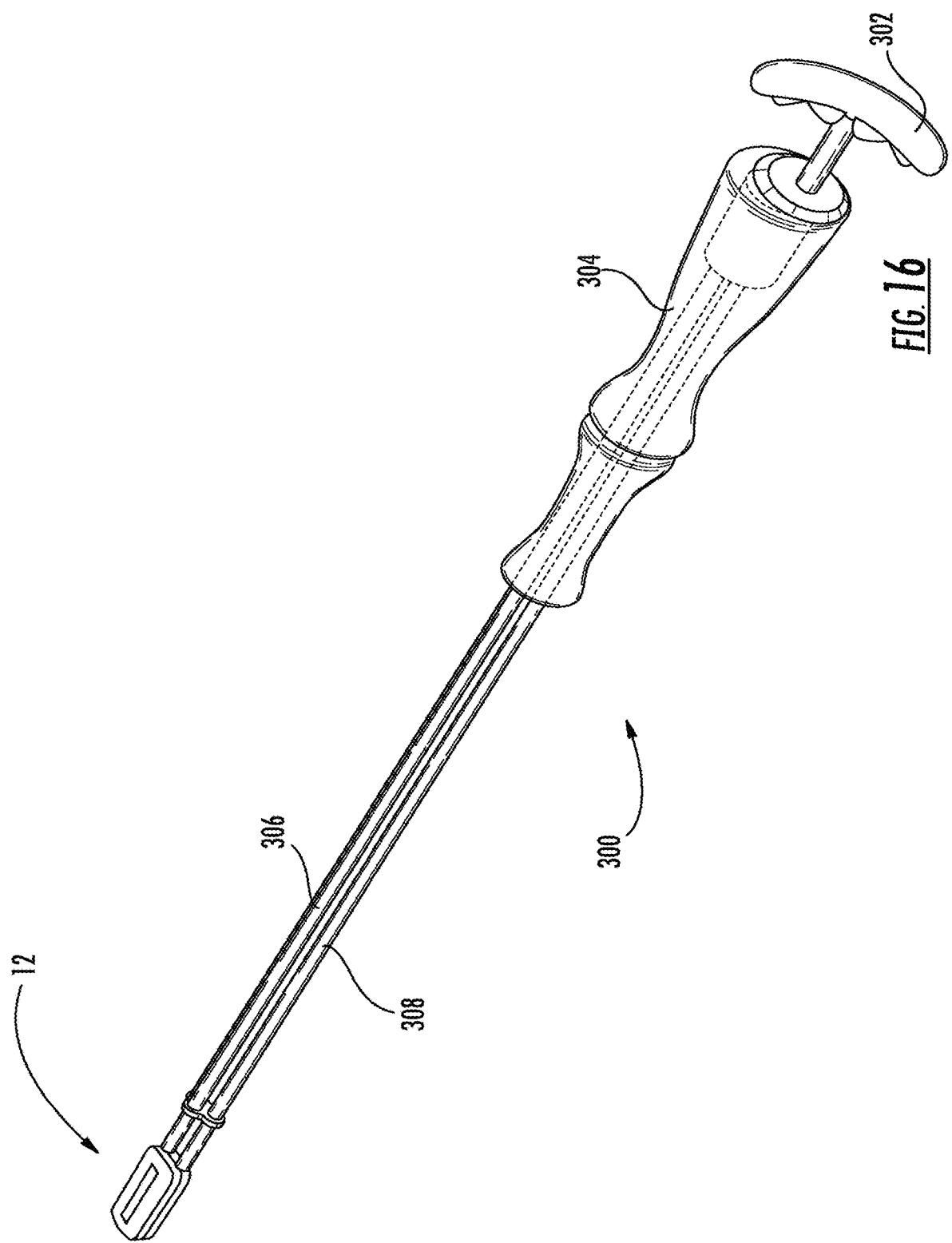

EXPANDABLE AND ADJUSTABLE LORDOSIS INTERBODY FUSION SYSTEM

RELATED APPLICATIONS

This application is a continuation-in-part of U.S. application Ser. No. 16/001,852 filed Jun. 6, 2018 entitled "EXPANDABLE AND ADJUSTABLE LORDOSIS INTERBODY FUSION SYSTEM," which is a continuation of U.S. application Ser. No. 15/859,241 filed Dec. 29, 2017 entitled "EXPANDABLE AND ADJUSTABLE LORDOSIS INTERBODY FUSION SYSTEM," issued as U.S. Pat. No. 10,188,527 on Jan. 29, 2019, which is a continuation of Ser. No. 14/473,200 filed Aug. 29, 2014 entitled "EXPANDABLE AND ADJUSTABLE LORDOSIS INTERBODY FUSION SYSTEM," issued as U.S. Pat. No. 9,889,019 on Feb. 13, 2018, which claims priority to U.S. provisional patent application No. 61/871,780 filed Aug. 29, 2013 entitled "EXPANDABLE LATERAL INTERBODY FUSION SYSTEM," the disclosures of all of which are hereby incorporated by reference in their entirety.

This application claims priority to U.S. provisional patent application No. 62/736,649 filed Sep. 26, 2018 entitled "EXPANDABLE AND ADJUSTABLE LORDOSIS INTERBODY FUSION SYSTEM," the disclosures of all of which are hereby incorporated by reference in their entirety.

TECHNICAL FIELD

The invention relates to surgical procedures and apparatus for treating lumbar back pain.

BACKGROUND OF THE INVENTION

Lumbar spinal fusion is a surgical procedure to correct problems relating to the human spine. It generally involves removing damaged disc and bone from between two vertebrae and inserting bone graft material that promotes bone growth. As the bone grows, the two vertebrae join, or fuse, together. Fusing the bones together can help make that particular area of the back more stable and help reduce problems related to nerve irritation at the site of the fusion. Fusions can be done at one or more segments of the spine.

Interbody fusion is a common procedure to remove the nucleus pulposus and or the annulus fibrosus that compose the intervertebral disc at the point of the back problem and replace it with a cage configured in shape and dimension to restore the distance between adjacent vertebrae to that of a proper condition. Surgical approaches to implement interbody fusion vary, and access to the patient's vertebral column can be made through the abdomen or back. One other surgical method for accomplishing lumbar spinal fusion in a less invasive way involves accessing the vertebral column through a small incision on the side of the body. This procedure is known as lateral lumbar interbody fusion.

Once the intervertebral disc is removed from the body during the lateral lumbar interbody fusion, the surgeon typically forces different trial implants between the vertebral endplates of the specific region to determine the appropriate size of the implant for maintaining a distance between the adjacent vertebrae. Another consideration is to maintain the natural angle between lumbar vertebral bodies to accommodate the lordosis, or natural curvature, of the spine. Therefore, during selection of a cage for implantation, both intervertebral disc height and lordosis must be considered. Prior art fusion cages are often pre-configured to have top and bottom surfaces angles to one another to accommodate the natural curvature of the spine. It is unlikely that these values can be determined precisely prior to the operation, which is a drawback in present procedures. Prepared bone graft is generally packed into the cage implant once it is properly sized and before it is inserted in between the vertebral bodies.

Present lateral interbody fusion cage devices are generally limited to providing height expansion functions, but not a lordotic adjustment capability. In implementing a trial-and-error approach to sizing and fitting the interbody fusion cage into the target region for the particular geometric configuration for that patient, the patient is subjected to significant invasive activity. The bone graft material is generally added and packed in to the fusion device after the desired height expansion has been reached and final adjustments made.

SUMMARY OF THE INVENTION

An embodiment of the device comprises an expandable housing comprised of opposing shell members. Movable tapered screw-like elements having an external helical thread are disposed in the housing and operably engage against the top and bottom shell members, urging them apart to cause expansion in the height of the housing. This function permits adjustment of the distance (height) between adjacent vertebrae when in place. The tapered members are disposed in a dual arrangement such that independent engagement of the tapered members along lateral portions of the top and bottom shells cause an angular tilt to the exterior surface of the housing when the wedge Members are moved to different degrees. This function permits adjustment in the angular relationship between adjacent vertebrae and assists the lordotic adjustment of the patient's spine. When the functions of the device are used in combination by the surgeon, the device provides an effective tool for in situ adjustment when performing lateral lumbar interbody fusion.

An embodiment of the device further comprises a track configuration within the housing for guiding the tapered external helical threaded members in their engagement with the top and bottom shell members. The track comprises raised elements on each of the interior surfaces of the top and bottom shell members that permit an interlocking engagement for lateral stability of the housing when in a contracted position. As the housing expands, the track area provides space for storage of bone graft material. One embodiment may provide for an elastic membrane to be positioned around the housing to prevent bone graft material from seeping out of the cage and to provide a compressive force around the cage to provide structural stability to the housing An embodiment of the device further comprises drive shafts for operating the tapered external helical threaded members. The drive shafts permit the surgeon, through the use of a supplemental tool, to manipulate the shafts which operatively move the tapered external helical threaded members in controlling the expansion of the housing and angular adjustment of the top and bottom shell members for in situ fitting of the interbody fusion device. A locking mechanism is provided for preventing rotation of the shafts when the tool is not engaged and after manipulation by the tool is completed. The tool also facilitates insertion of bone graft material into the fusion body during in situ adjustment.

An embodiment of the present invention provides a surgeon with the ability to both expand the fusion cage and adjust the lordotic angle of the fusion cage in situ during operation on a patient and to introduce bone graft material at the operation site while the device is in place. This embodiment of the present invention therefore provides a fusion cage having geometric variability to accommodate the spinal condition unique to each patient.

Embodiments of the present invention therefore provide an interbody cage device for use in lateral lumbar interbody fusion procedures that combines the functions of height expansion for adjusting the distance between adjacent vertebrae with lordotic adjustment to control the angular relationship between the vertebrae. Embodiments of the inventive interbody cage device further provide a storage capacity for containing bone graft material in the interbody cage device as disc height and lordotic adjustment takes place in situ.

The present invention also provides a device that may be used in environments other than in interbody fusion applications. It may generally be used to impart a separating effect between adjacent elements and to impart a variable angular relationship between the elements to which it is applied.

An embodiment of a spinal implant device for placement between vertebral bodies includes a housing, at least one screw member in the housing, and at least one drive shaft operably engageable with the screw member. The housing includes a first shell member and a second shell member. At least the first shell member has step tracking comprising a plurality of individual riser members for receiving the at least one screw member. The height of the plurality of individual riser members may change along the step tracking. The drive shaft may be operable to rotate the at least one screw member, causing the at least one screw member to move on the plurality of individual riser members. The at least one screw member comprises an external helical thread having a thickness configured to fit in the gaps between adjacent individual riser members, and is engageable with the first and second shell members, whereby the first and second shell members move relative to each other in response to the rotation of the at least one screw member to effect an expansion of the housing or a contraction of the housing from the expansion by reversing the rotation of the at least one screw member.

An embodiment of a spinal implant device comprises a housing, a first pair of screw members and a second pair of screw members in the housing, a first drive shaft operably engageable with the first pair of screw members and a second drive shaft operably engageable with the second pair of screw members. The housing comprises a first shell member and a second shell member each having a plurality of individual riser members. The plurality of individual riser members of the first and second shell members define a first step tracking run along a first lateral area of the housing and a second step tracking run along a second lateral area of the housing. The height of the plurality of individual riser members change along the first and second step tracking runs. The first drive shaft is operable to rotate the first pair of screw members causing the first pair of screw members to move along the first step tracking run. The second drive shaft is operable to rotate the second pair of screw members causing the second pair of screw members to move along the second step tracking run. The first and second drive shafts are operable independently of each other. The first and second pairs of screw members each comprises an external helical thread having a thickness configured to fit in a gap between adjacent individual riser members and is engageable with the first and second shell members, whereby the first and second shell members move relative to each other in response to rotation of the first and/or second pairs of screw members to effect an expansion of the housing or a contraction of the housing from the expansion by reversing the rotation of the first and/or second pairs of screw members, wherein a degree of expansion or contraction of the first lateral area of the housing is independently adjustable relative to a degree of expansion or contraction of the second lateral area of the housing when the first and second pairs of screw members are rotated independently to different positions on the first and second step tracking runs.

These and other features of the present invention are described in greater detail below in the section titled DETAILED DESCRIPTION OF THE INVENTION.

BRIEF DESCRIPTION OF THE DRAWINGS FIGURES

An embodiment of the present invention is described herein with reference to the following drawing figures, with greater emphasis being placed on clarity rather than scale:

FIG. 5 is a perspective view of a tapered external helical threaded member.

FIG. 5A is a view in side elevation from the side of the tapered external helical threaded member.

FIG. 5B is a view in side elevation from the front of the tapered external helical threaded member.

FIG. 6 is a cross-sectional view of the device taken along lines 6-6 in FIG. 1.

FIG. 9B is a perspective view of the drive shafts and thrust bearings.

FIG. 9C is a top plan view in cross section of the area of engagement of the drive shafts with the thrust bearings.

FIG. 11B is a top plan view of yet another embodiment of the device.

FIG. 14 is a view taken along lines 14-14 in FIG. 11A.

Figure 15A:
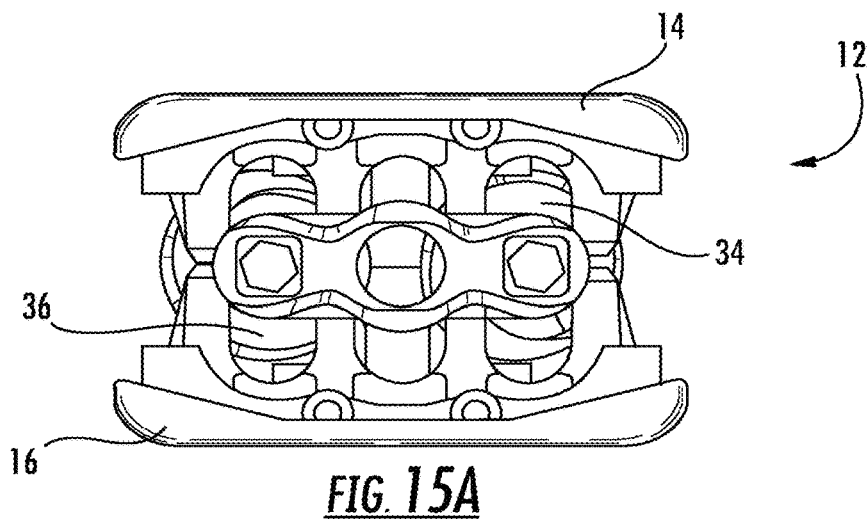
Figure 15B:
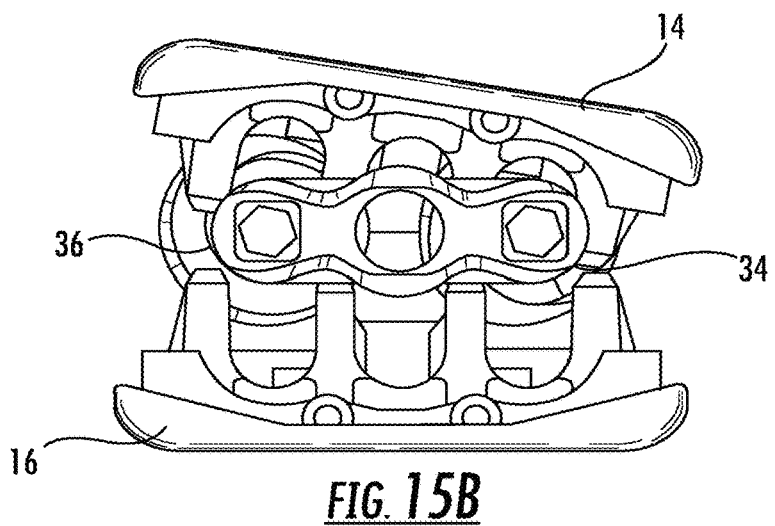
Figure 15C:
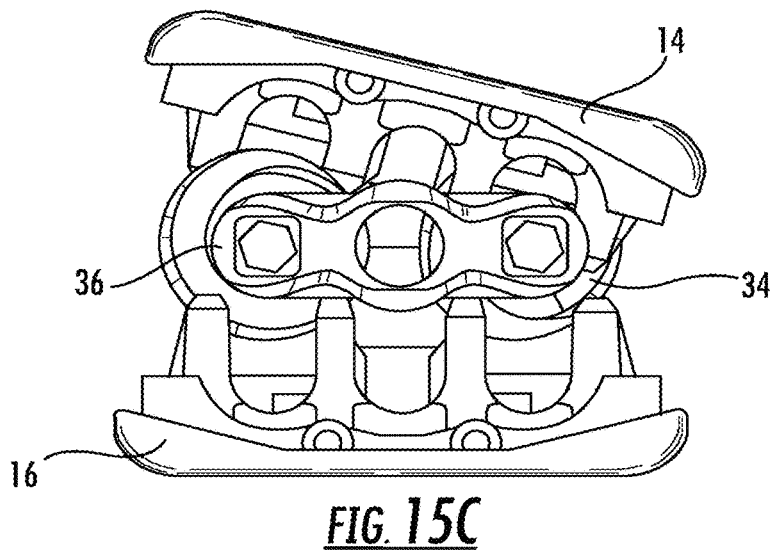

FIGS. 15A-C are a series of views in side elevation taken from the end of the device as it undergoes expansion showing the lordotic effect.

FIG. 16 is a perspective view of the operating tool.

Figure 17:
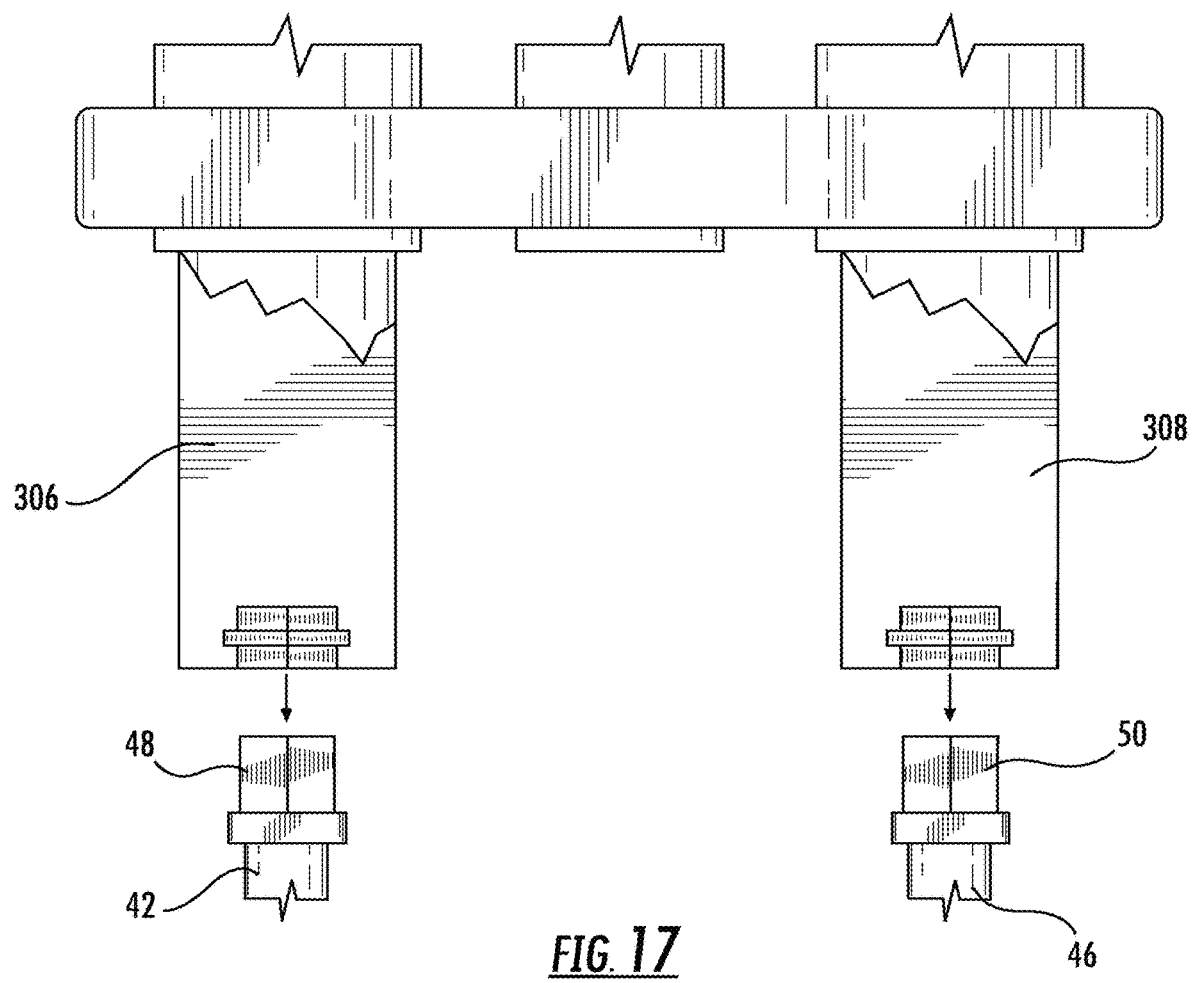

FIG. 17 is a view showing a manner of attachment of the operating tool to the drive shafts of the device.

Figure 18:
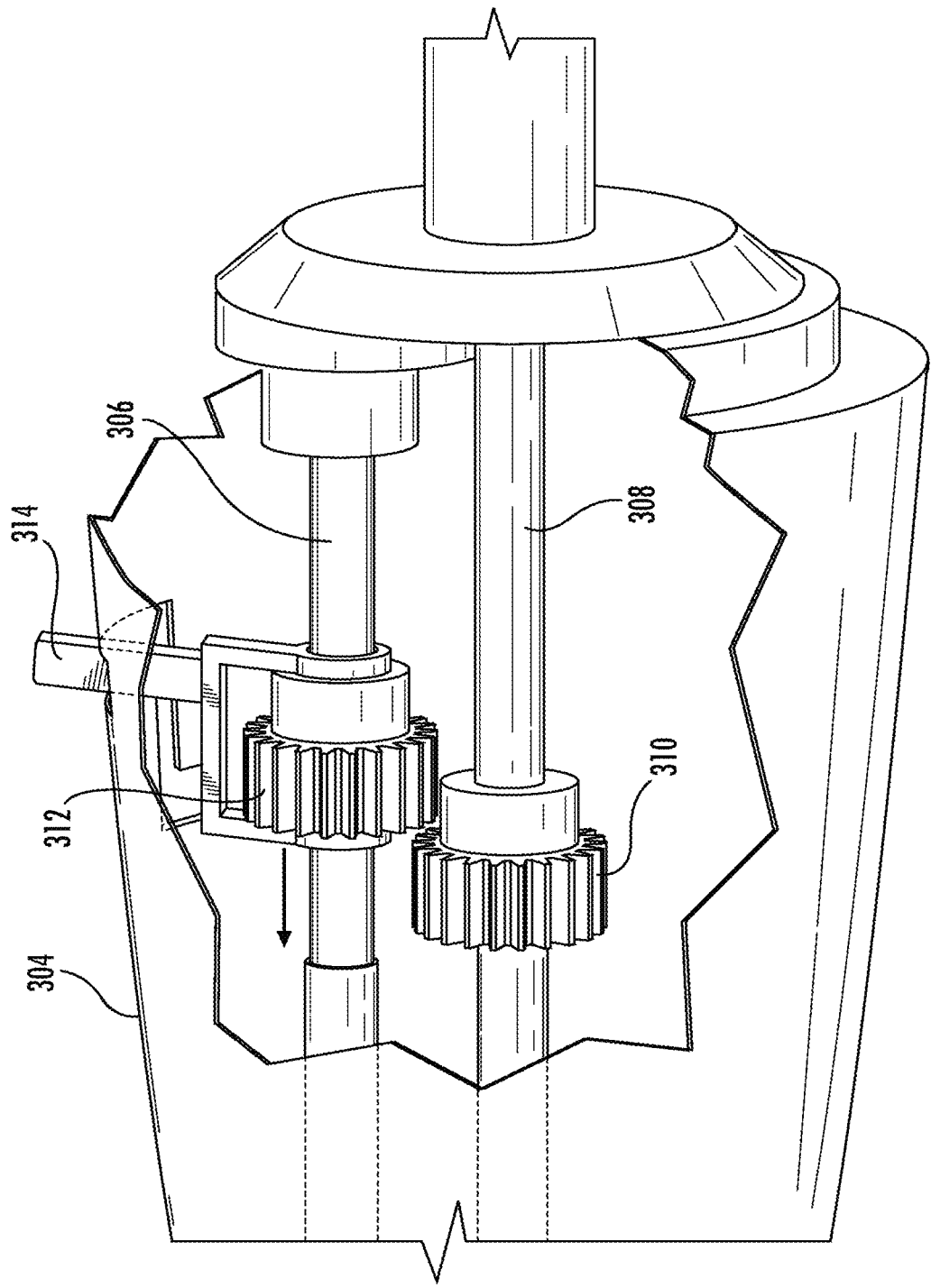

FIG. 18 is a breakaway perspective view of the handle of the operating tool.

Figure 19:
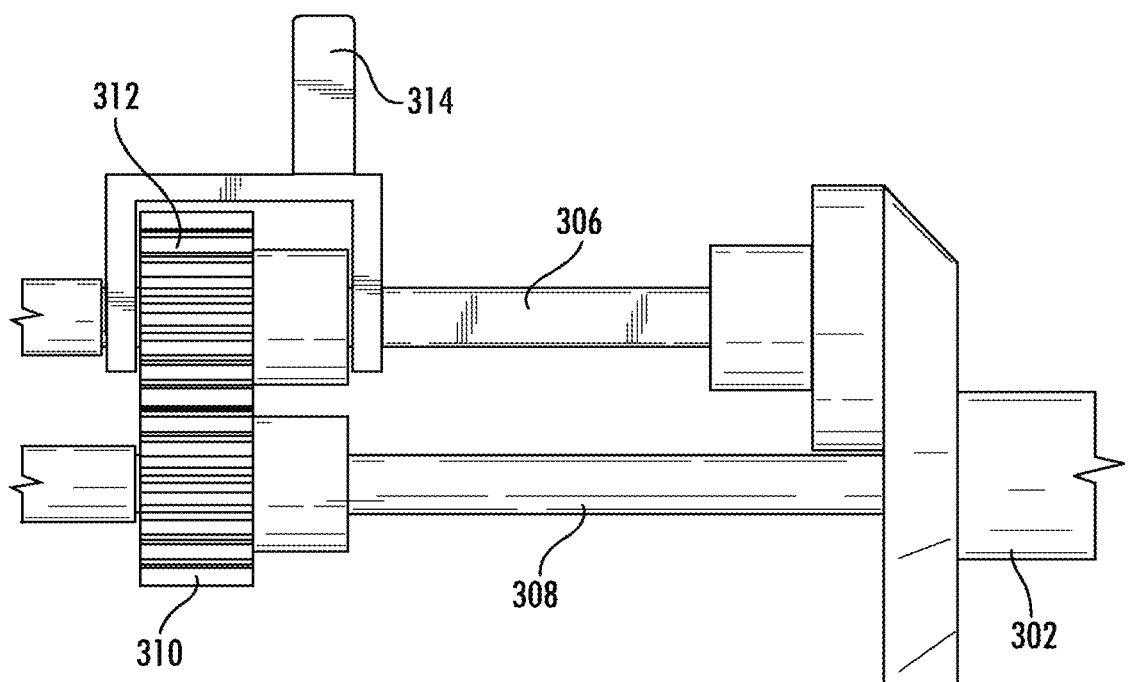

FIG. 19 is a perspective view of gears in the handle engaged for operation of both drive shafts.

Figure 20:
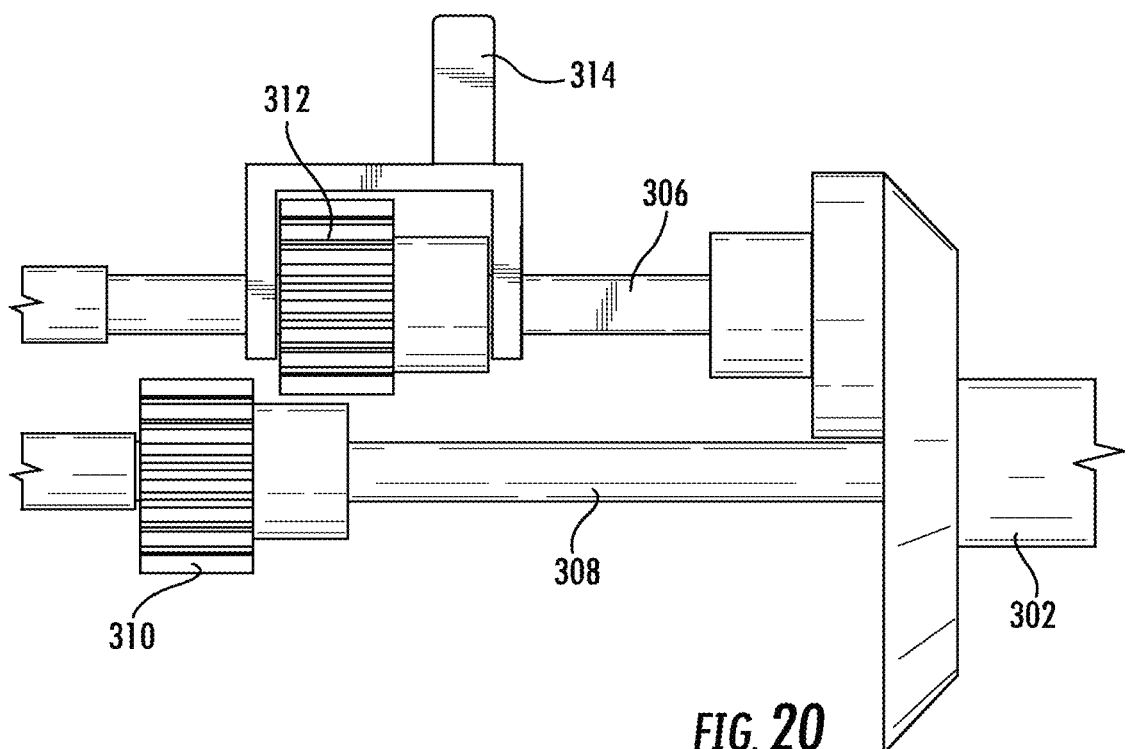

FIG. 20 is a perspective view of gears in the handle disengaged for operation of a single drive shaft.

Figure 21:
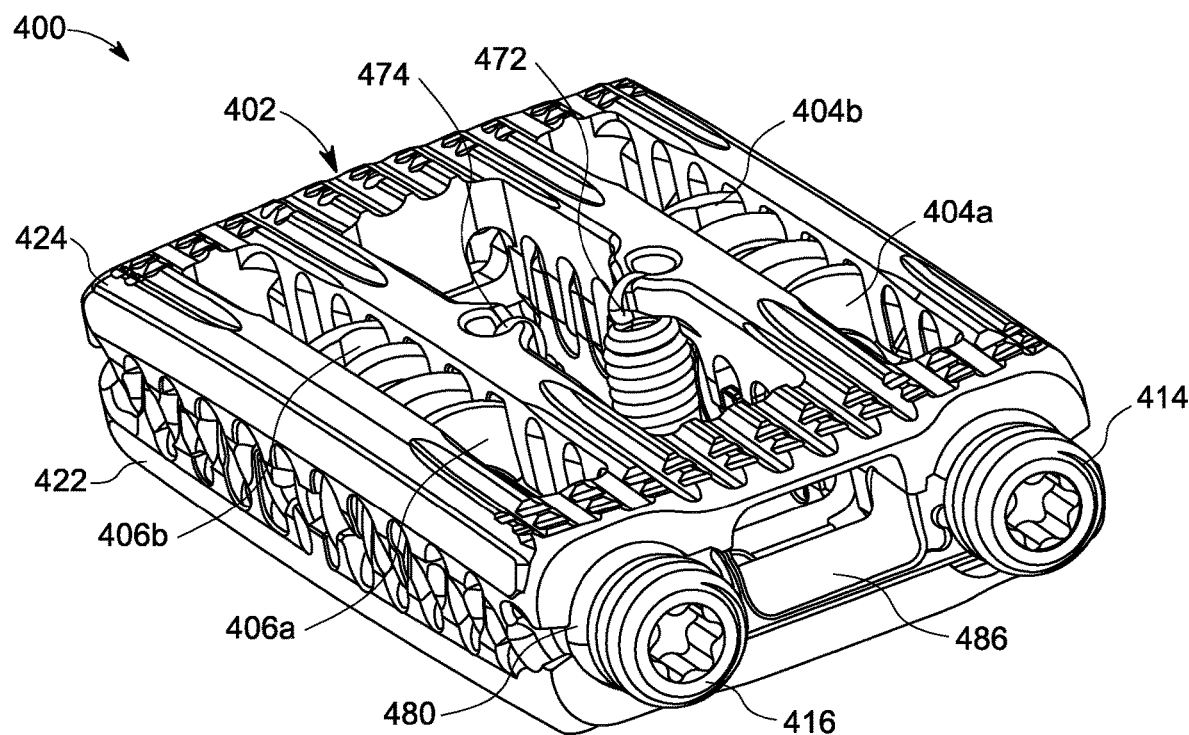

FIG. 21 is a perspective top view of an exemplary spinal implant device according to embodiments of the disclosure.

Figure 22:
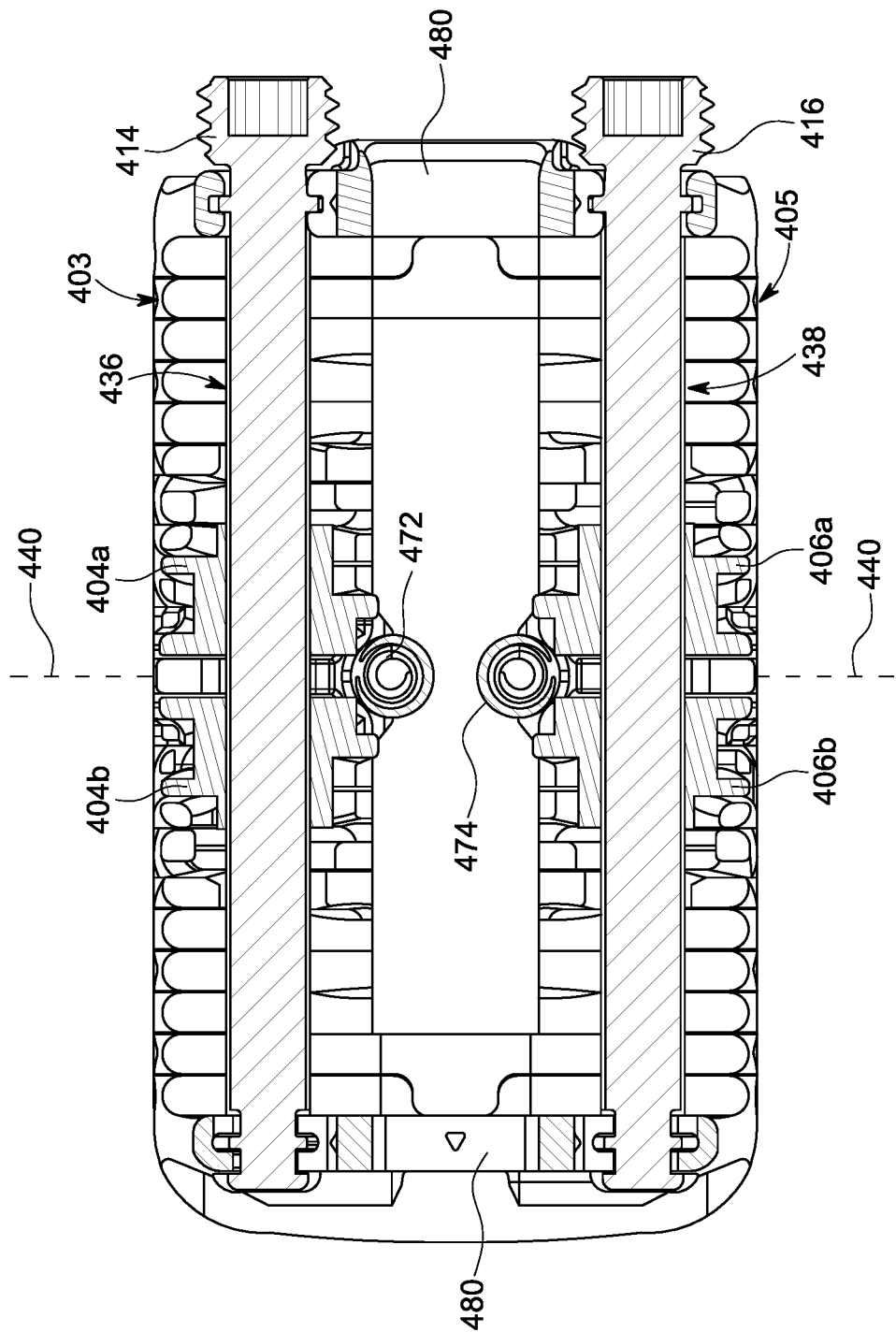

FIG. 22 is a cross-sectional view of an exemplary spinal implant device according to embodiments of the disclosure.

Figure 23:
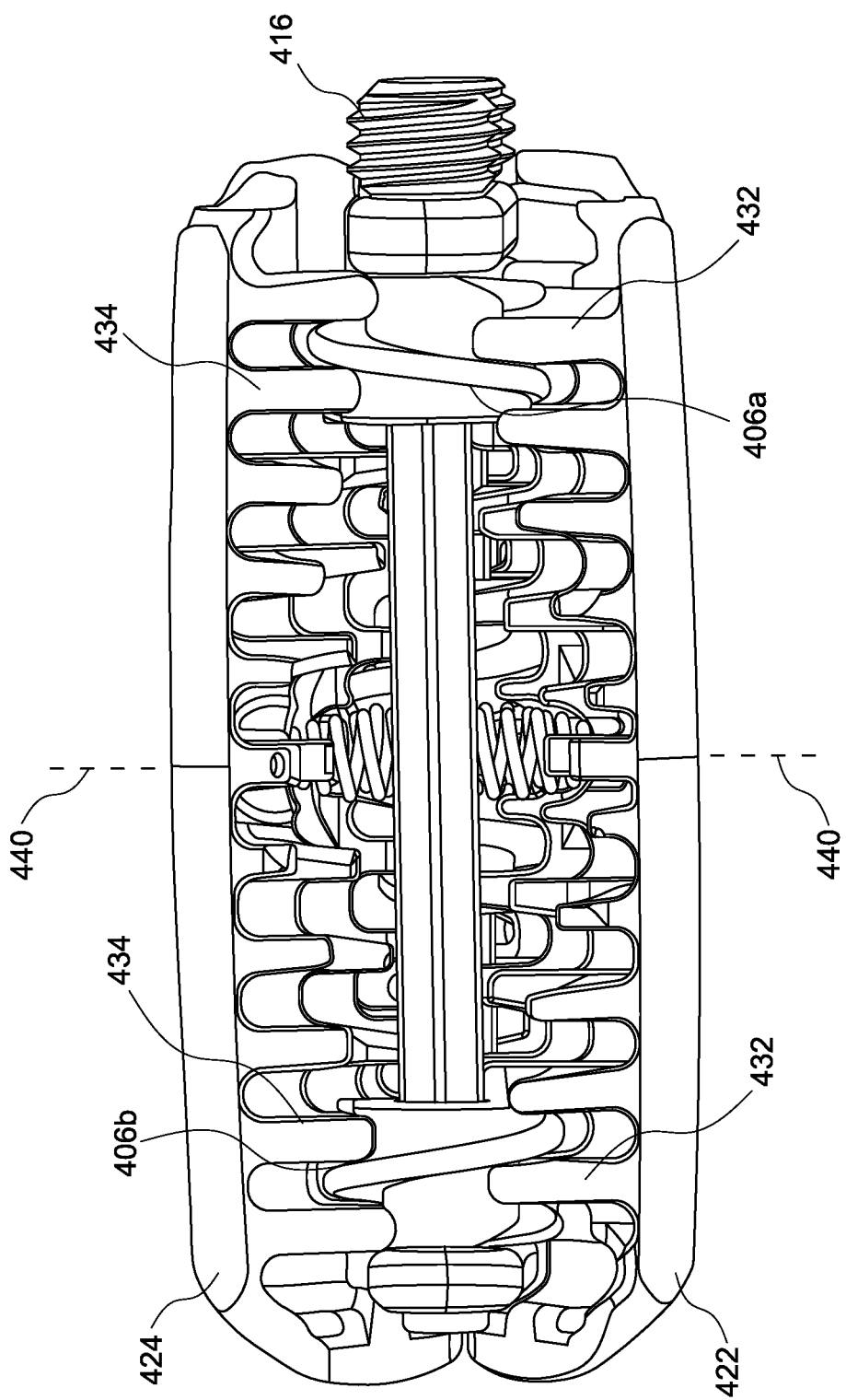

FIG. 23 is a perspective side view of an exemplary spinal implant device according to embodiments of the disclosure.

Figure 24:
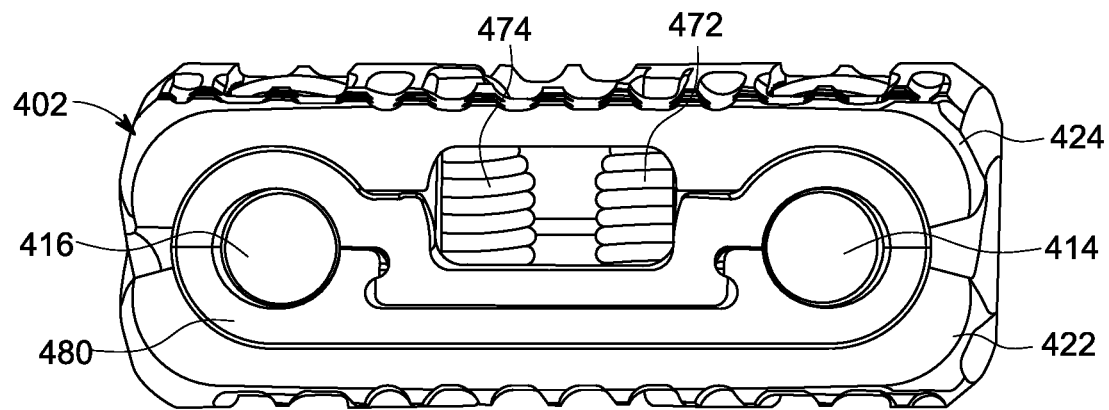

FIG. 24 is a cutaway, front view of an exemplary spinal implant device according to embodiments of the disclosure.

Figure 25:
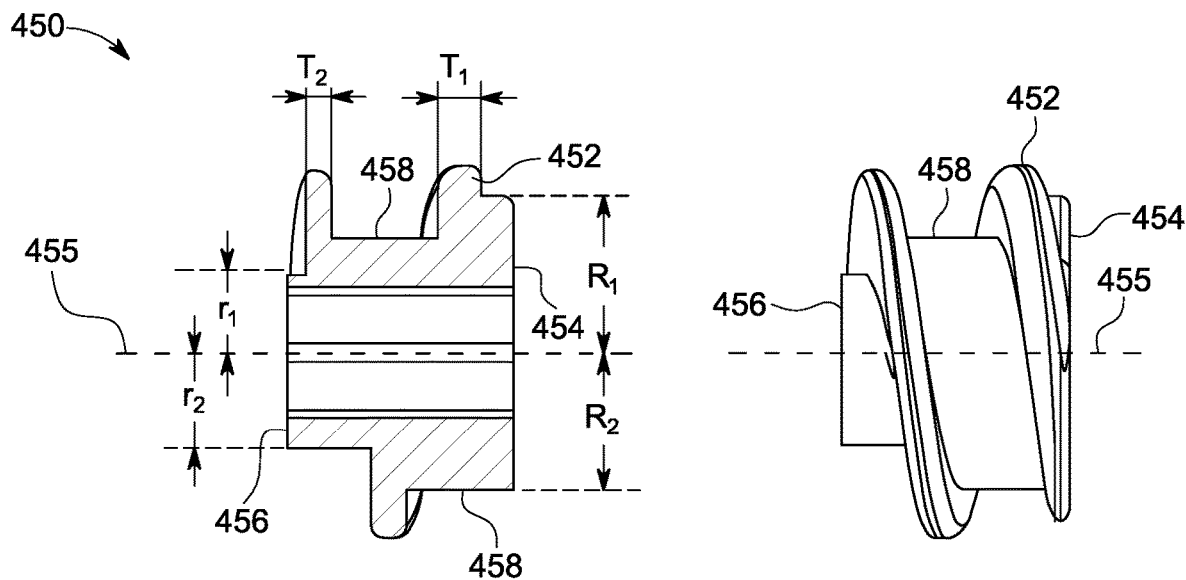

FIG. 25 schematically shows a tapered screw member according to embodiments of the disclosure.

Figure 26:
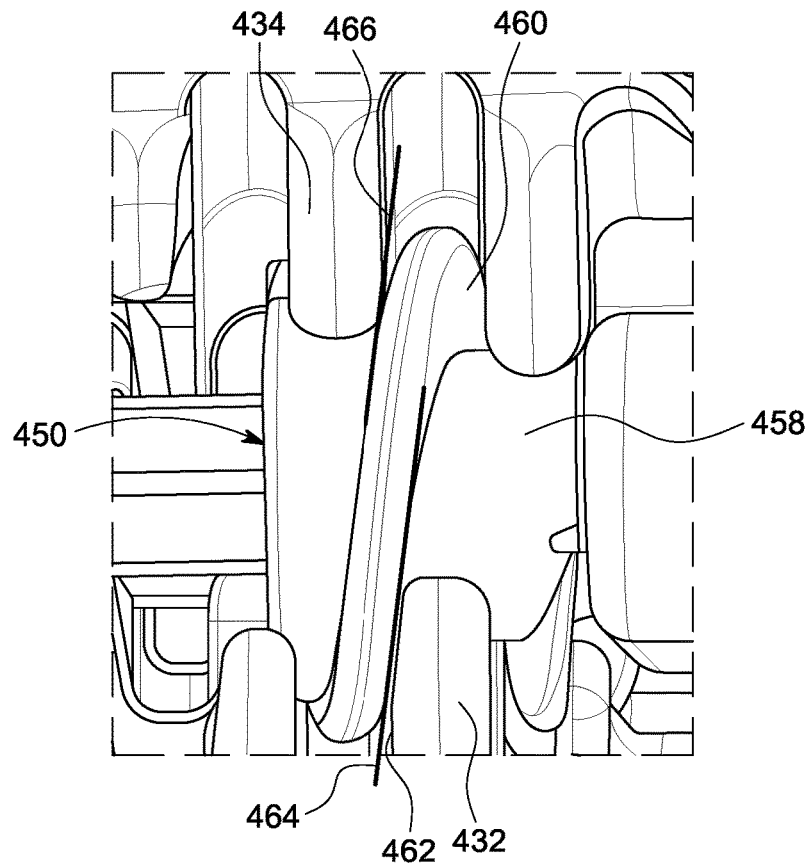

FIG. 26 schematically shows a tapered screw member engaging individual riser members according to embodiments of the disclosure.

Figure 27:
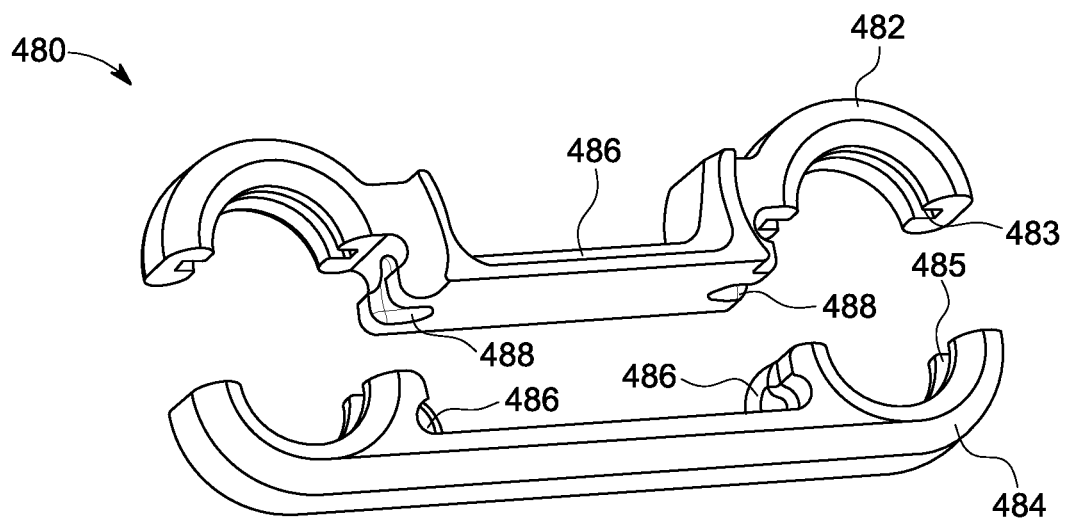

FIG. 27 is an exploded view of a thrust bearing member according to embodiments of the disclosure.

Figure 28:
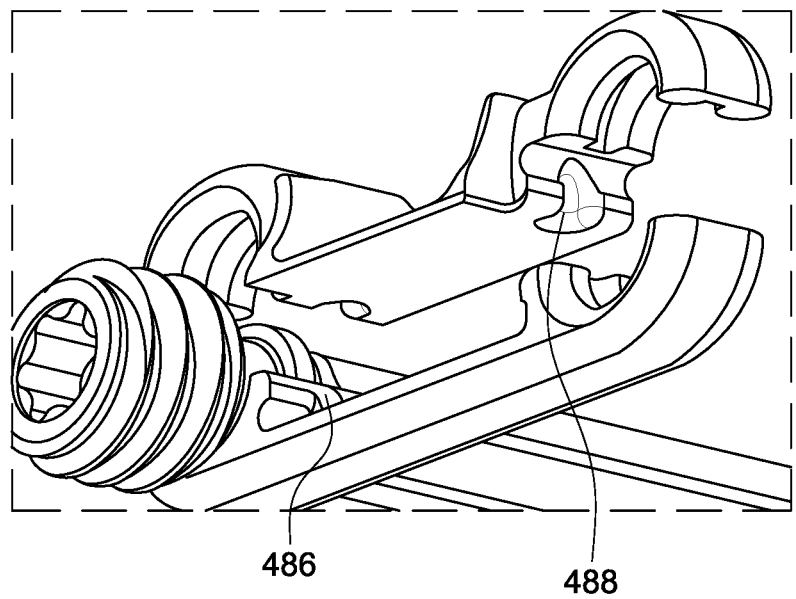

FIG. 28 is a cutaway view of a thrust bearing member in relation to other components of an exemplary spinal implant device according to embodiments of the disclosure.

Figure 29:
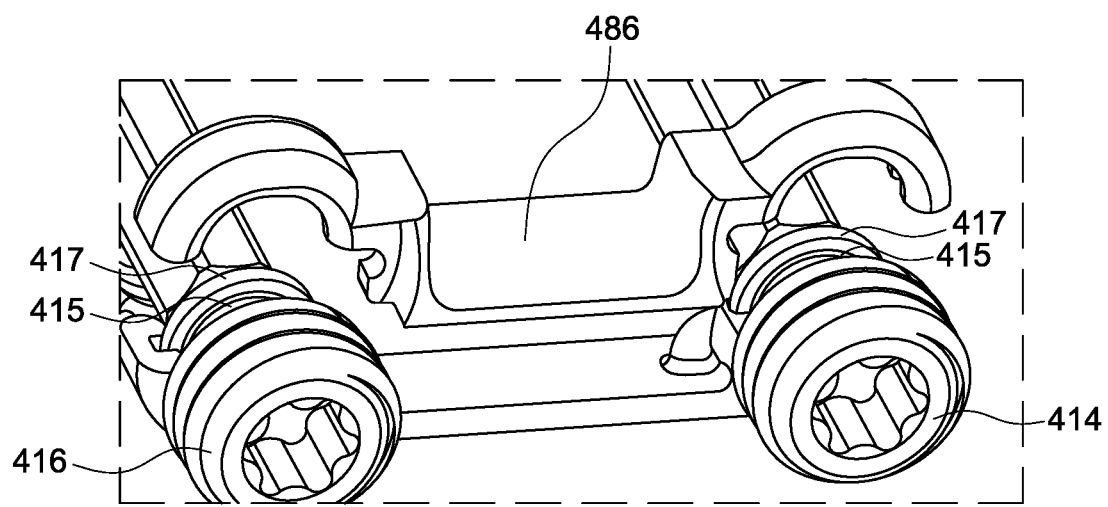

FIG. 29 is cutaway view of a thrust bearing member in relation to other components of an exemplary spinal implant device according to embodiments of the disclosure.

Figure 30:
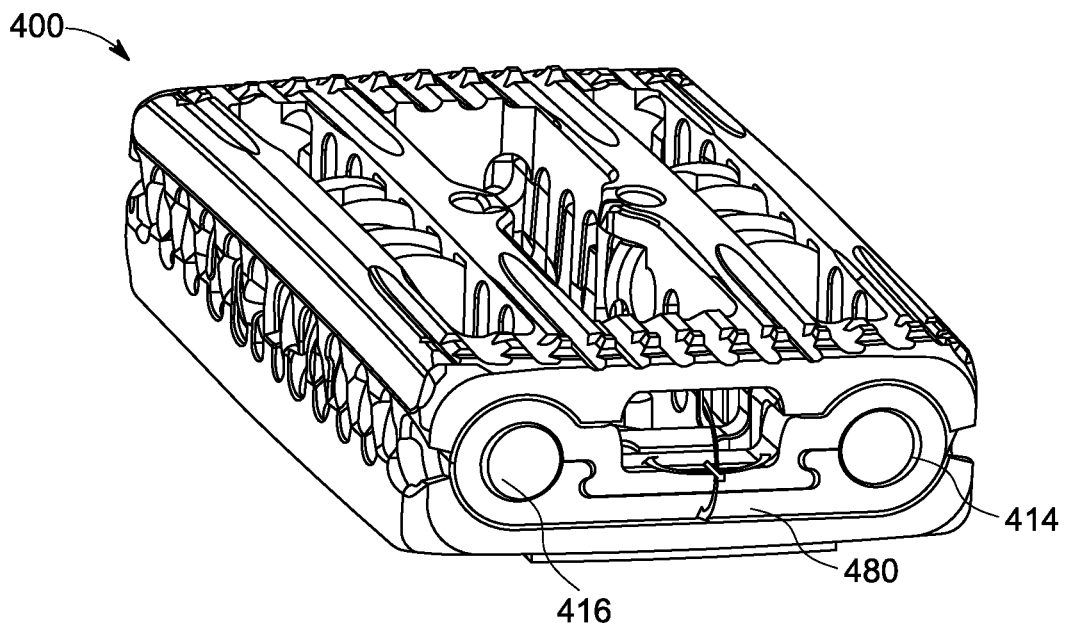

FIG. 30 is a perspective view of an exemplary spinal implant device in a parallel configuration according to embodiments of the disclosure.

Figure 31:
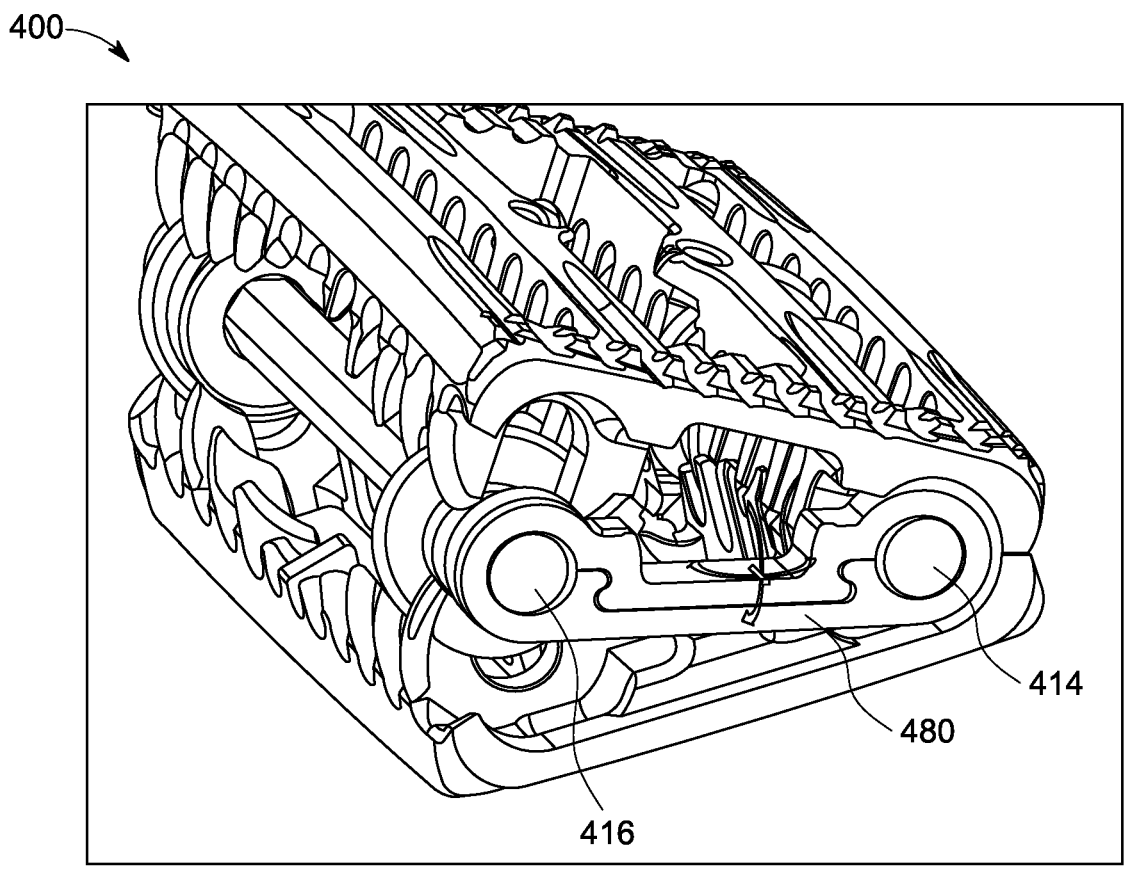

FIG. 31 is a perspective view of an exemplary spinal implant device in a lordosis configuration according to embodiments of the disclosure

DETAILED DESCRIPTION OF THE INVENTION

Figure 1:
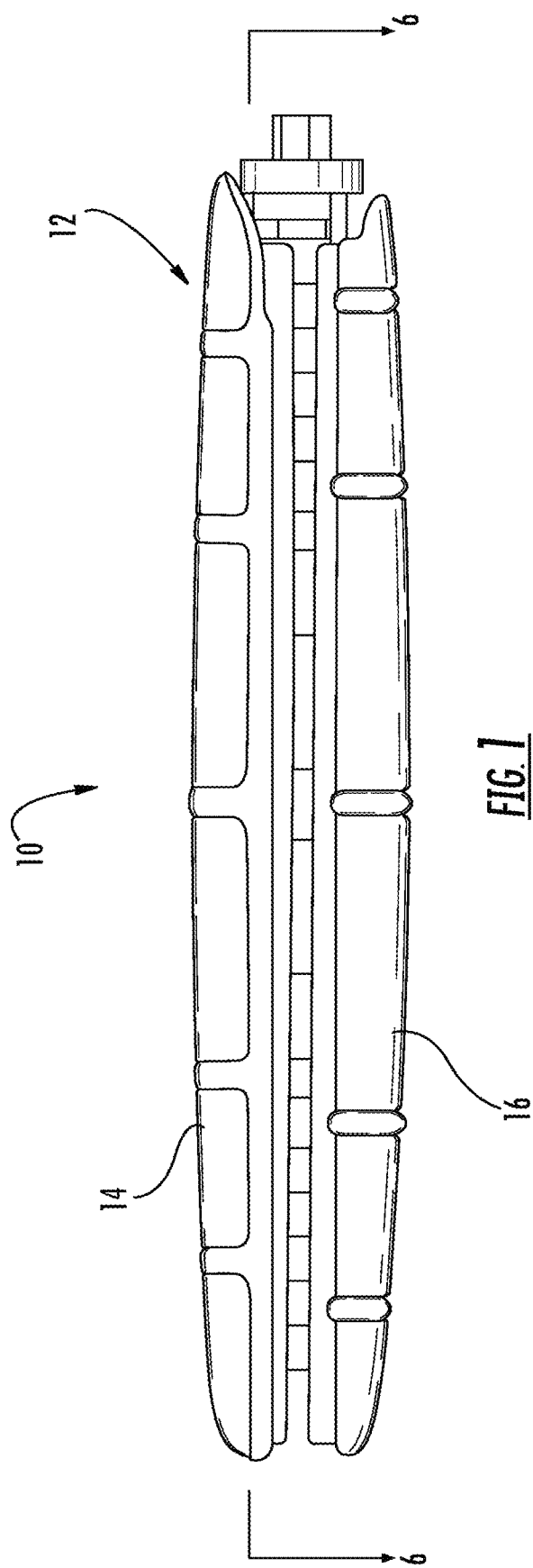
FIG. 1 is a view in side elevation from the side of the expandable shell device.
Figure 2:
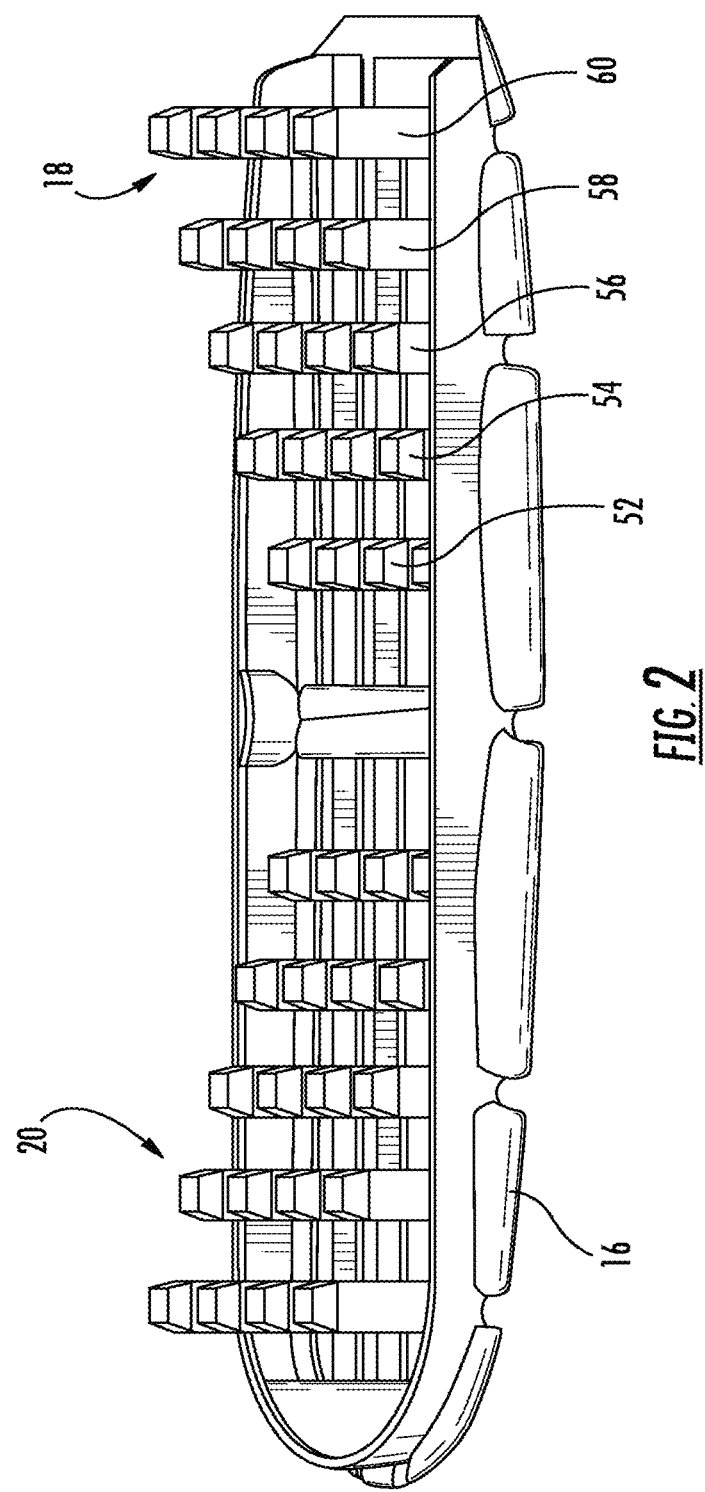
FIG. 2 is a perspective view of a bottom section of the expandable shell.
Figure 3:
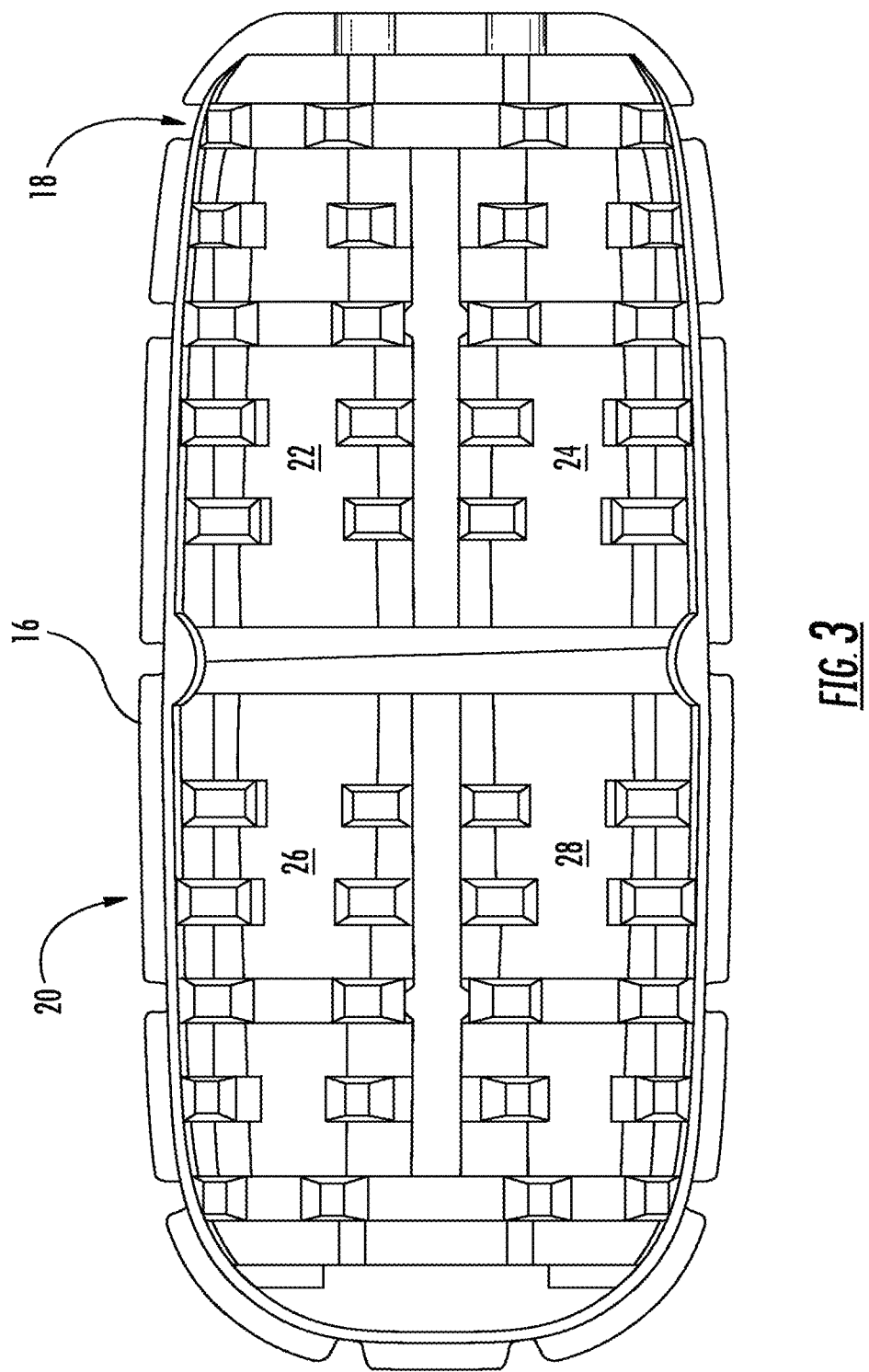
FIG. 3 is a top plan view of the bottom section of the expandable shell.
Figure 4:
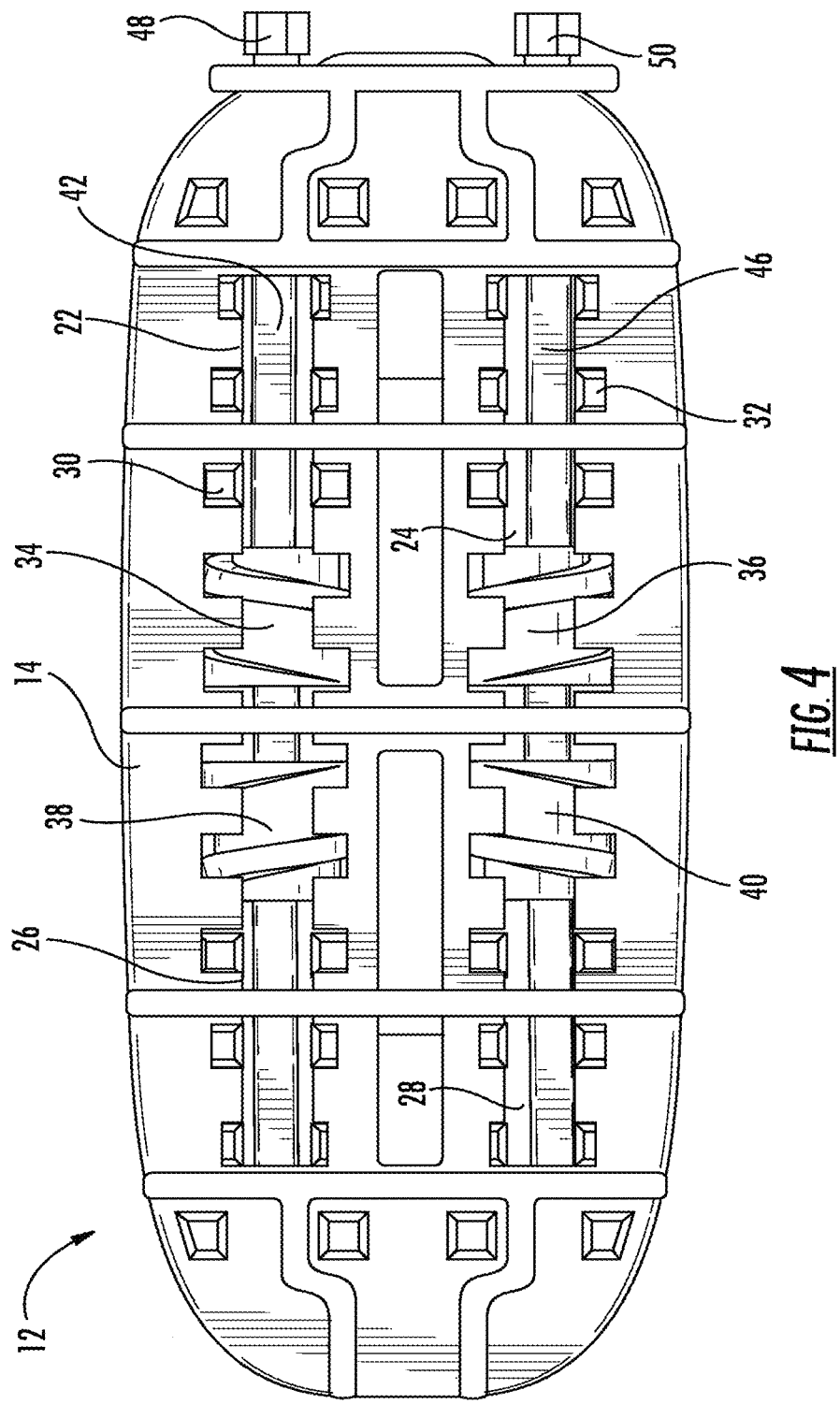
FIG. 4 is a top plan view of the expandable shell device.

With reference to the drawings, an interbody fusion body device is herein described, shown, and otherwise disclosed in accordance with various embodiments, including preferred embodiments, of the present invention. The interbody fusion device 10 is shown generally in FIG. 1. It is comprised of a housing 12 having a top shell 14 and a bottom shell 16. The overall housing may have a length of 50 mm and a width of 20 mm, as an example. The shell material may be comprised of a suitable material, such as titanium alloy (Ti-6AL-4V), cobalt chromium, or polyether ether ketone (PEEK). Other materials may be suitable that can provide sufficient compositional integrity and that have suitable biocompatible qualities. The interior of the shells is configured with a cascading step tracking 18 and 20 placed along their lateral edges. As shown in FIG. 2, step tracking 18 begins towards the midpoint of an inner surface of bottom shell 16 with successive track steps increasing in height as the tracking extends to a first end of bottom shell 16. Correspondingly, step-tracking 20 begins towards the midpoint of the inner surface of bottom shell 16 with successive track steps increasing in height as that portion of the tracking extends to a second opposite end of bottom shell 16. Step tracking 18 comprises dual track runs 22 and 24 while step tracking 20 comprises dual track runs 26 and 28 as shown in FIG. 3. Corresponding step tracking 30 and 32 is provided on top shell 14 as shown in FIG. 4. When the device is in its fully compressed state where top shell 14 lies adjacent to bottom shell 16, as shown in FIG. 1, step tracking 18 intermeshes with step tracking 30 and step tracking 20 intermeshes with step tracking 32.

The respective track runs comprise a series of risers, or track steps, which are spaced apart to receive the threads of tapered external helical threaded members. The tapered external helical threaded members provide a wedging action for separating the top and bottom shell thereby increasing the height of the housing to effect expansion between the vertebral bodies in which the device is placed. As shown in FIG. 4, track run 22 receives tapered external helical threaded member 34, track run 24 receives tapered external helical threaded member 36, track run 26 receives tapered external helical threaded member 38, and track run 28 receives tapered external helical threaded member 40. Track run 22 aligns collinearly with track run 26 such that the travel of tapered external helical threaded members 34 and 38 within the respective track runs occurs within that collinear alignment. The thread orientation of tapered external helical threaded members 34 and 38 are opposite of each other such that their rotation will result in opposite directional movement with respect to each other. As shown in FIG. 4, a drive shaft 42 runs along the collinear span of track runs 22 and 26 and passes through tapered external helical threaded members 34 and 38. Shaft 42 has a square cross-sectional configuration for engaging and turning the tapered external helical threaded members. As shown in FIG. 5, the central axial opening 44 of the tapered external helical threaded members are configured to receive and engage the shaft 42. Shaft 42 may alternatively comprise any shape for effectively creating a spline, such as a hexagonal shape, and central axial openings 44 may comprise a corresponding configuration for receiving that shape. As shaft 42 is rotated by its end 48 in a clockwise direction, tapered external helical threaded members 34 and 38 are rotated and their respective thread orientations cause the screws to travel apart from each other along track run 22 and track run 26, respectively. Correspondingly, as shaft 42 is rotated by its end 48 in a counter-clockwise direction, tapered external helical threaded members 34 and 38 are caused to travel towards each other along track run 22 and track run 26, respectively.

Similarly, track run 24 aligns collinearly with track run 28 such that the travel of tapered external helical threaded members 36 and 40 within the respective track runs occurs within that collinear alignment. The thread orientation of tapered external helical threaded members 36 and 40 are opposite of each other such that their rotation will result in opposite directional movement with respect to each other. Also, shaft 46 passes through and engages tapered external helical threaded members 36 and 40. However, the orientation of tapered external helical threaded members 36 and 40 is reversed from the orientation of tapered external helical threaded members 34 and 38. Under this orientation, as shaft 46 is rotated by its end 50 in a counter-clockwise direction, tapered external helical threaded members 36 and 40 are rotated and their respective thread orientations cause the screws to travel apart from each other along track run 24 and track run 28, respectively. Correspondingly, as shaft 46 is rotated by its end 50 in a clockwise direction, tapered external helical threaded members 36 and 40 are caused to travel towards each other along track run 24 and track run 28, respectively.

Figure 7A:
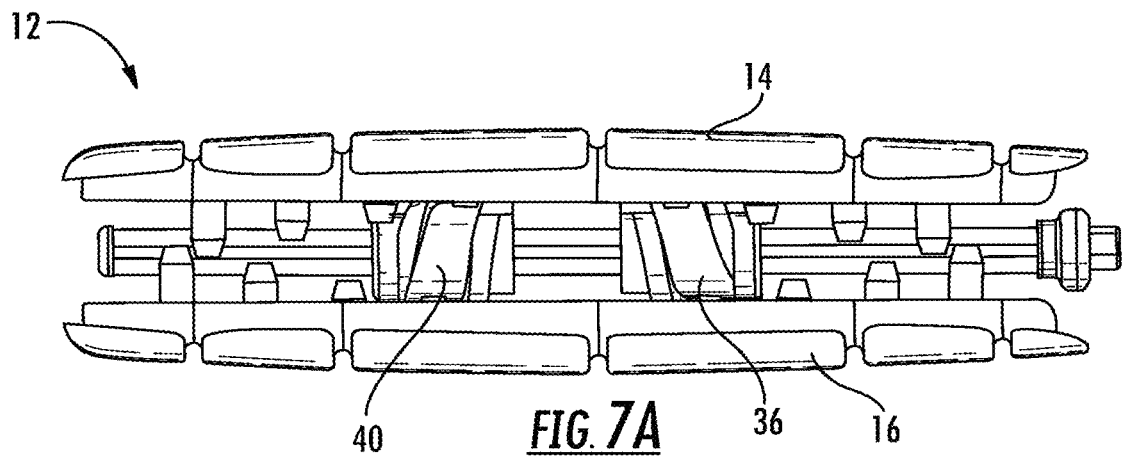
FIGS. 7A-7C are a series of views in side elevation of the device as it undergoes expansion.
Figure 7B:
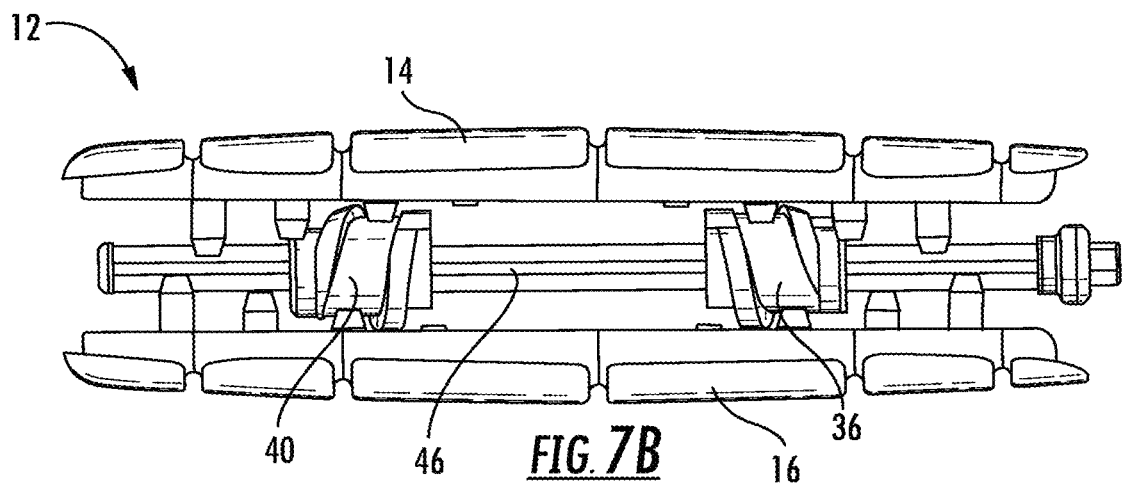
Figure 7C:
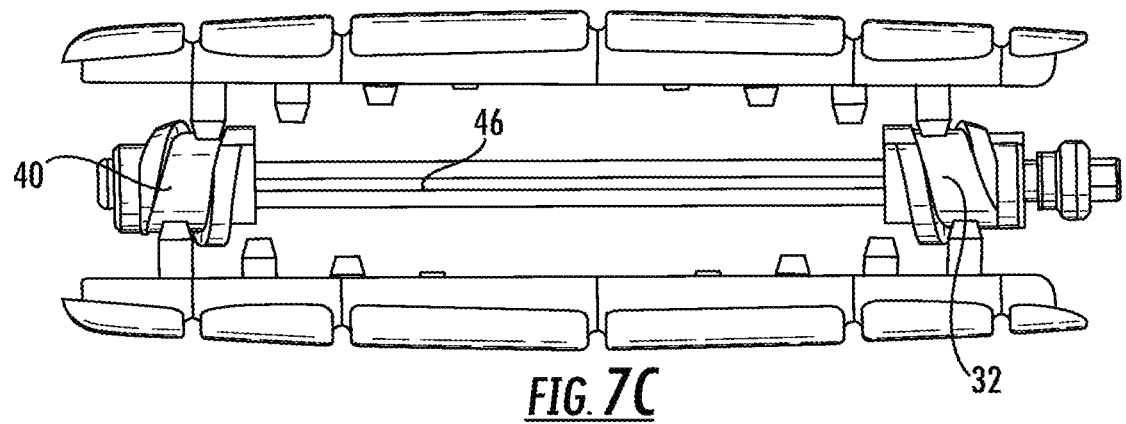

As shown in FIG. 2, the step tracking is configured with a cascading series of risers of increasing height. For example, each track run has risers 52-60 as shown for step tracking 18 in FIG. 2. As the thread of a tapered external helical threaded member travels into the gap between riser 52 and 54, the positional height of the tapered external helical threaded member body, as supported on risers 52 and 54, increases within the housing 12. As the tapered external helical threaded member continues to travel along the track run, its thread passes from the gap between risers 52 and 54 and enters the gap between risers 54 and 56 which raises the tapered external helical threaded member body further within housing 12 as it is supported on risers 54 and 56. As the tapered external helical threaded member continues its travel along the remainder of the step risers 58 and 60 its positional height increases further. As the positional height of the tapered external helical threaded member body increases, it urges top shell 14 apart from bottom shell 16 as shown in the series of FIGS. 7A-7C.

Figure 10:
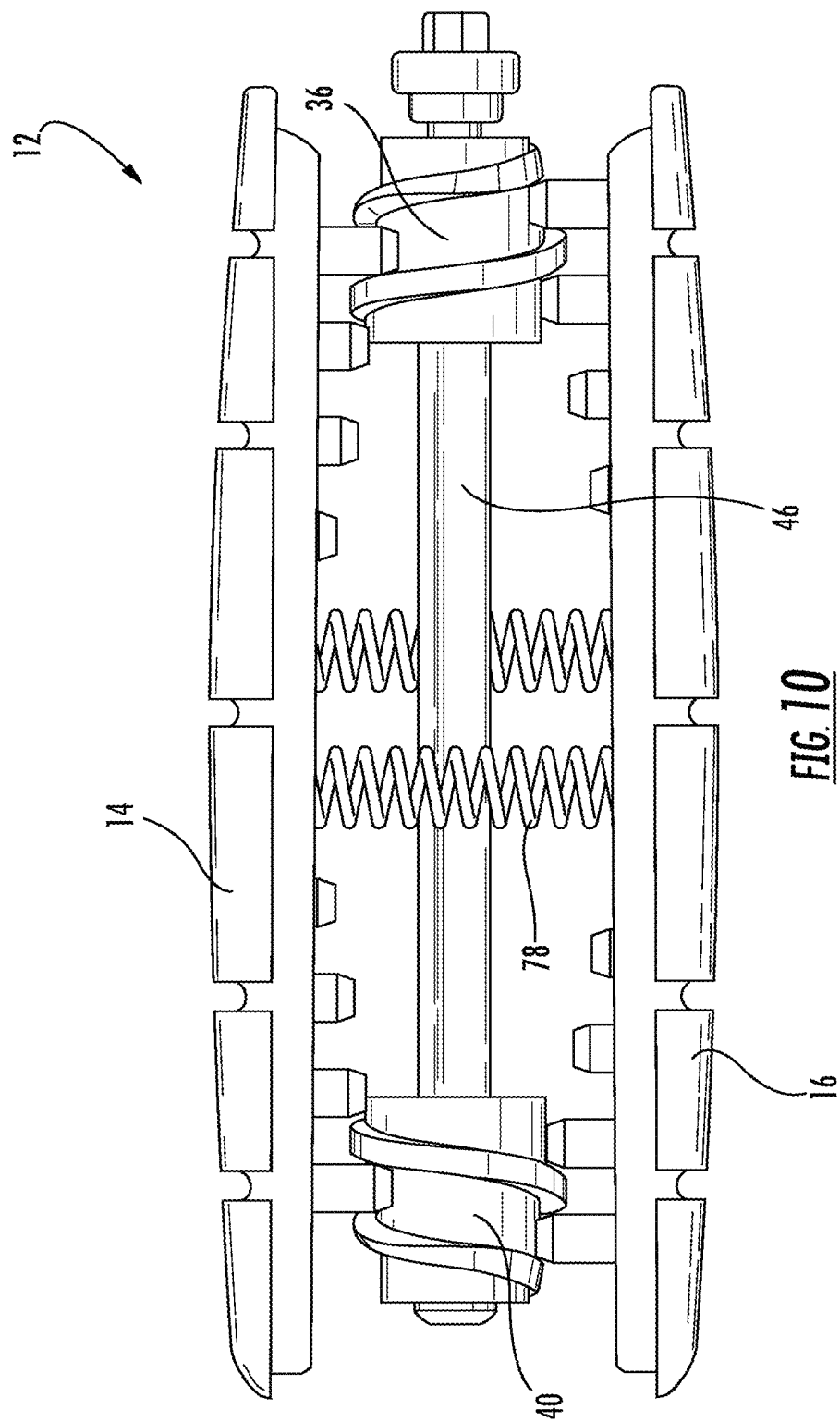
FIG. 10 is a side elevation view of the housing as expanded.

The combined effect of rotating the tapered external helical threaded members to cause their movement towards the outer ends of the respective track runs causes an expansion of the housing 12 as shown in FIG. 7. The fully expanded shell is shown in FIG. 10. The housing 12 may be contracted by reversing the movement of the tapered external helical threaded members such that they travel back along their respective track runs towards the midpoint of the housing. The housing will optimally provide expansion and contraction to give the implant device a height over a range of around approximately 7.8 mm to 16.15 mm in the present embodiment. The device of this embodiment of the invention can be adapted to provide different expansion dimensions.

Figure 8:
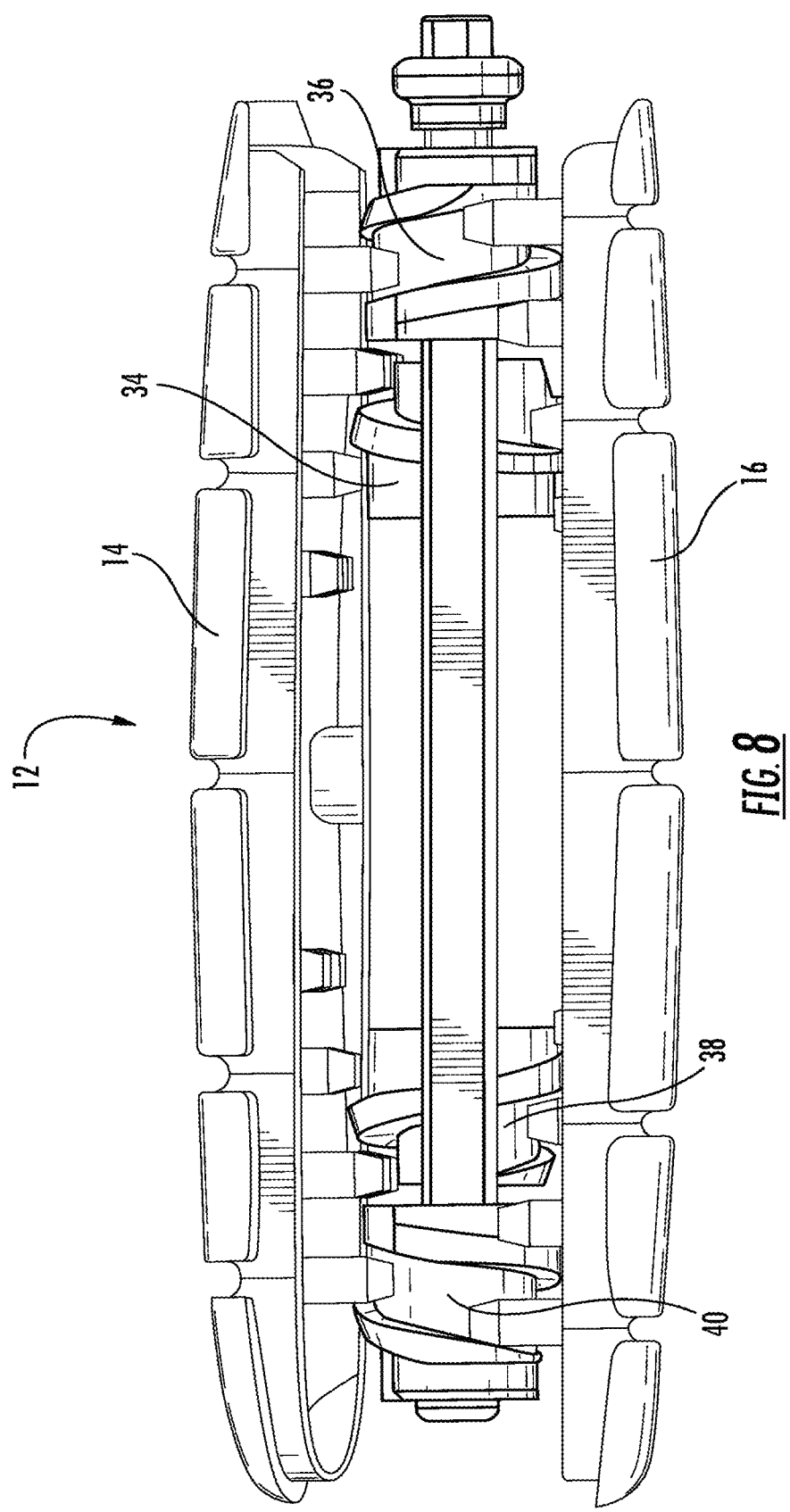
FIG. 8 is a view in side elevation of the device showing an expansion of the device to accommodate a lordotic effect.

The pairs of tapered external helical threaded members in each collinear dual track run may be rotated independently of the pair of tapered external helical threaded members in the parallel track run. In this arrangement, the degree of expansion of that portion of the housing over each collinear track run may be varied to adjust the lordotic effect of the device. As an example shown in FIG. 8, tapered external helical threaded members 36 and 40 have been extended to a particular distance along track run 24 and track run 28, respectively, causing the top shell 14 to separate from bottom shell 16 thereby expanding housing 12. Tapered external helical threaded members 34 and 38 have been extended to a lesser distance along parallel track run 22 and 26, respectively, causing that portion of the top shell over track runs 22 and 26 to separate from bottom shell to a lesser degree. The series of FIGS. 15A-15C show this effect where tapered external helical threaded members 36 and 40 are extended apart from each other in further increasing increments where the tapered external helical threaded members 34 and 38 maintain the same relative distance to each other.

In FIG. 15A, the respective positioning of the set of tapered external helical threaded members 36-40 is approximately the same as the set of tapered external helical threaded members 34-38 in their respective tracking. In this position, the top shell 14 is essentially parallel with bottom shell 16. In FIG. 15B, the set of tapered external helical threaded members 36-40 move further distally apart along their tracking as the set of tapered external helical threaded members 34-38 remains at their same position in FIG. 15A. In this setting, the lateral edge of top shell 14 along which tapered external helical threaded members 36 and 40 travel is moved higher with respect to the lateral edge of top shell 14 along which tapered external helical threaded members 34 and 38 travel, giving a tilt to top shell 14 with respect to bottom shell 16. In FIG. 15C, the set of tapered external helical threaded members 36-40 move even further distally apart along their tracking with respect to that of the set of tapered external helical threaded members 34-38, giving an even greater tilt to top shell 14 with respect to bottom shell 16. Through the independent movement of the respective tapered external helical threaded member sets, the device can achieve a lordotic effect of between 0° and 35° in the present embodiment. The device of this embodiment of the invention can be adapted to provide different lordotic tilt dimensions.

The tapered external helical threaded members have a configuration comprising a body profile that has an increasing minor diameter from $D_{r1}$ to $D_{r2}$ as shown in FIG. 5. The threads 33 have a pitch to match the spacing between the riser elements 52-60 in the tracking runs as shown in FIG. 4. Threads 33 can have a square profile to match the configuration between the risers, but other thread shapes can be used as appropriate. The increasing diameter and tapering aspect of the helical threaded members cause top shell 14 and bottom shell 16 to move apart as described above. The contact at the tops of the risers 52-60 is made at the minor diameter of the helical threaded member.

Figure 9A:
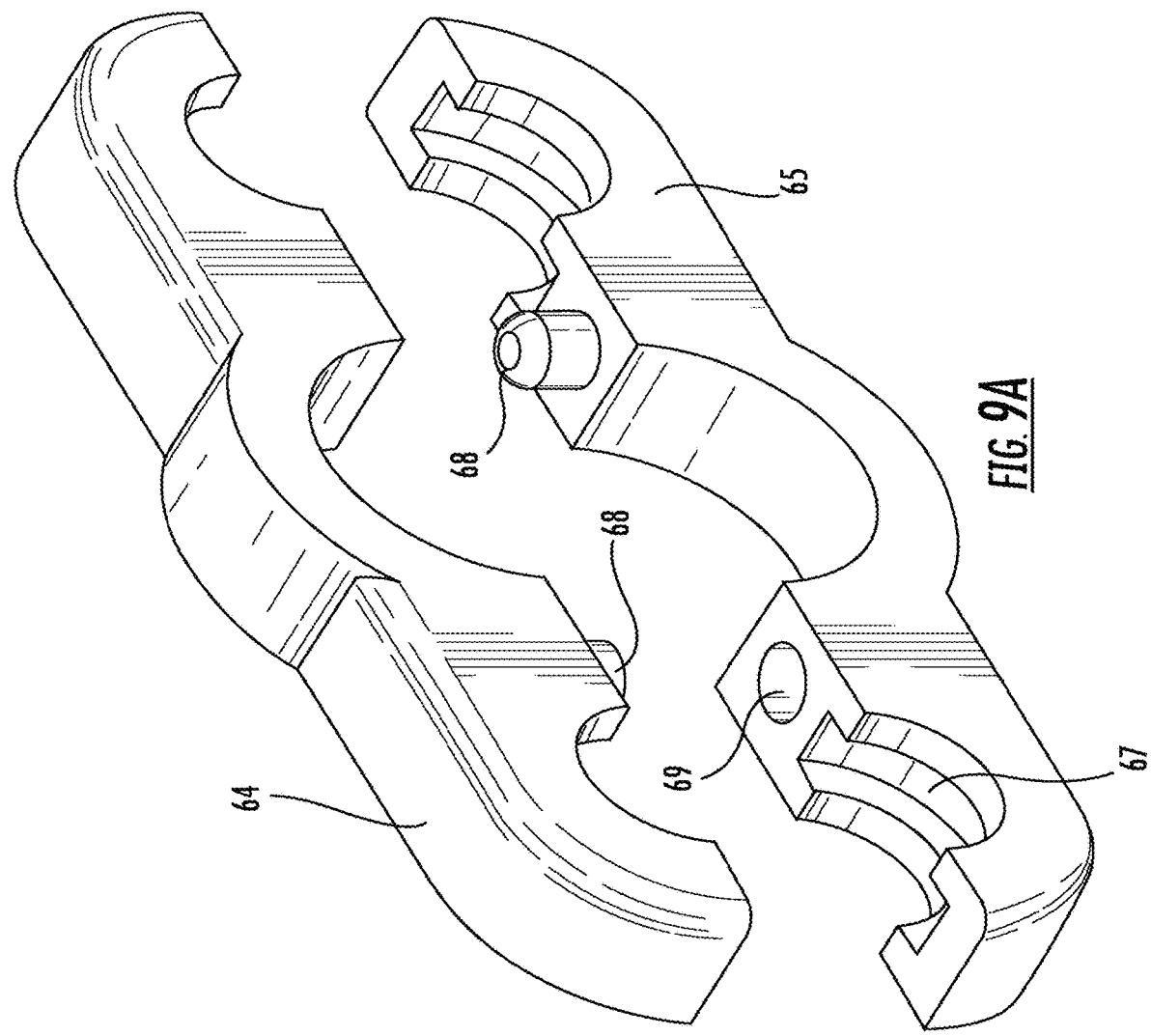
FIG. 9A is a perspective expanded view of thrust bearing for the drive shaft.

Thrust bearings are provided to limit the axial direction motion of the drive shafts within shell 12. As shown in FIG. 9A, thrust bearing 62 comprises a two-piece yoke configuration that mate together and press-fit around ends of the shafts. The top part 64 of the thrust bearing yoke defines openings for receiving a round portion 66 of the shaft ends. In FIG. 9C, square shaft 42 has a rounded portion 66 of lesser diameter than the square portion of the shaft. A mating piece 65 of the thrust bearing engages with top part 64 to encircle the rounded portion 66 of drive shaft 42.

Pin elements 68 in the top portion 64 and bottom portion 65 engages a corresponding hole 69 in the mating piece to provide a press fit of the thrust bearing around the shaft. Journal grooves 67 can also be provided in thrust bearing 62. Shaft 42 can have an annular ridge 63 around its rounded portion 66 which is received in journal groove 67 as shown in FIG. 9C. A thrust bearing is provided at each end of the drive shafts as shown in FIG. 9B. As shown in FIG. 6, the thrust bearings restrict the axial movement of the drive shafts in the housing.

Figure 12A:
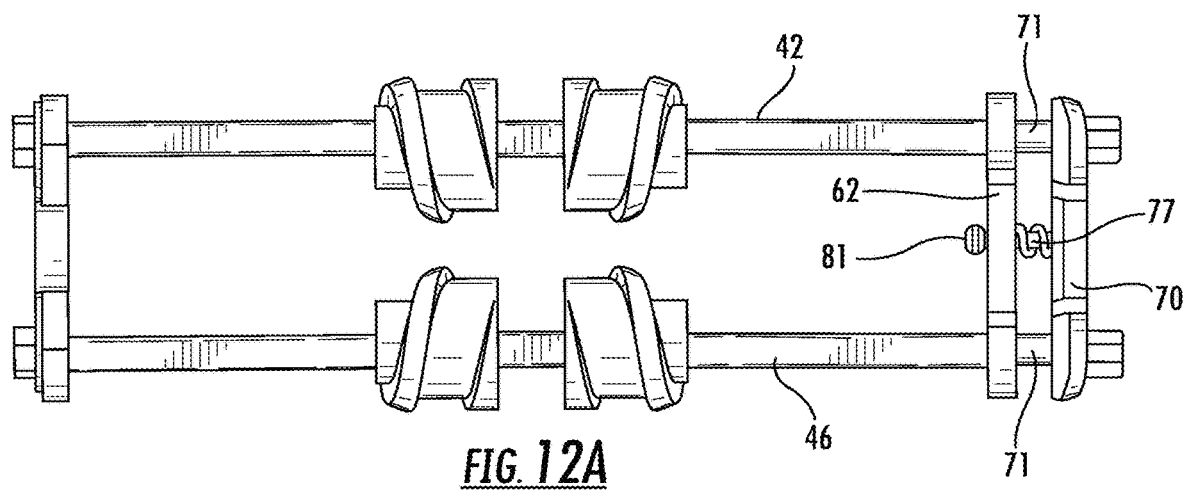
FIG. 12A is a top plan view of the drive shafts disengaged by the locking mechanism.
Figure 12B:
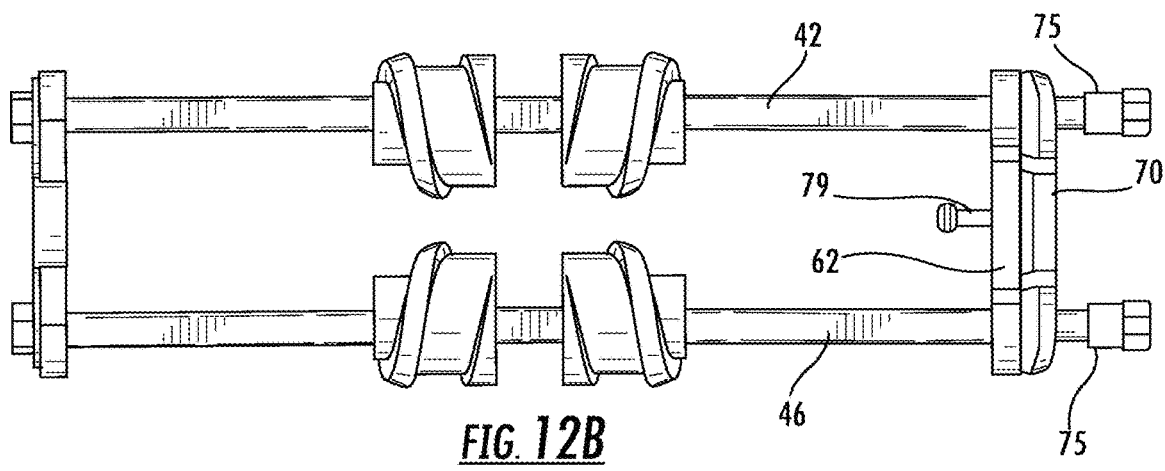
FIG. 12B is a top plan view of the drive shafts engaged by the locking mechanism.
Figure 13A:
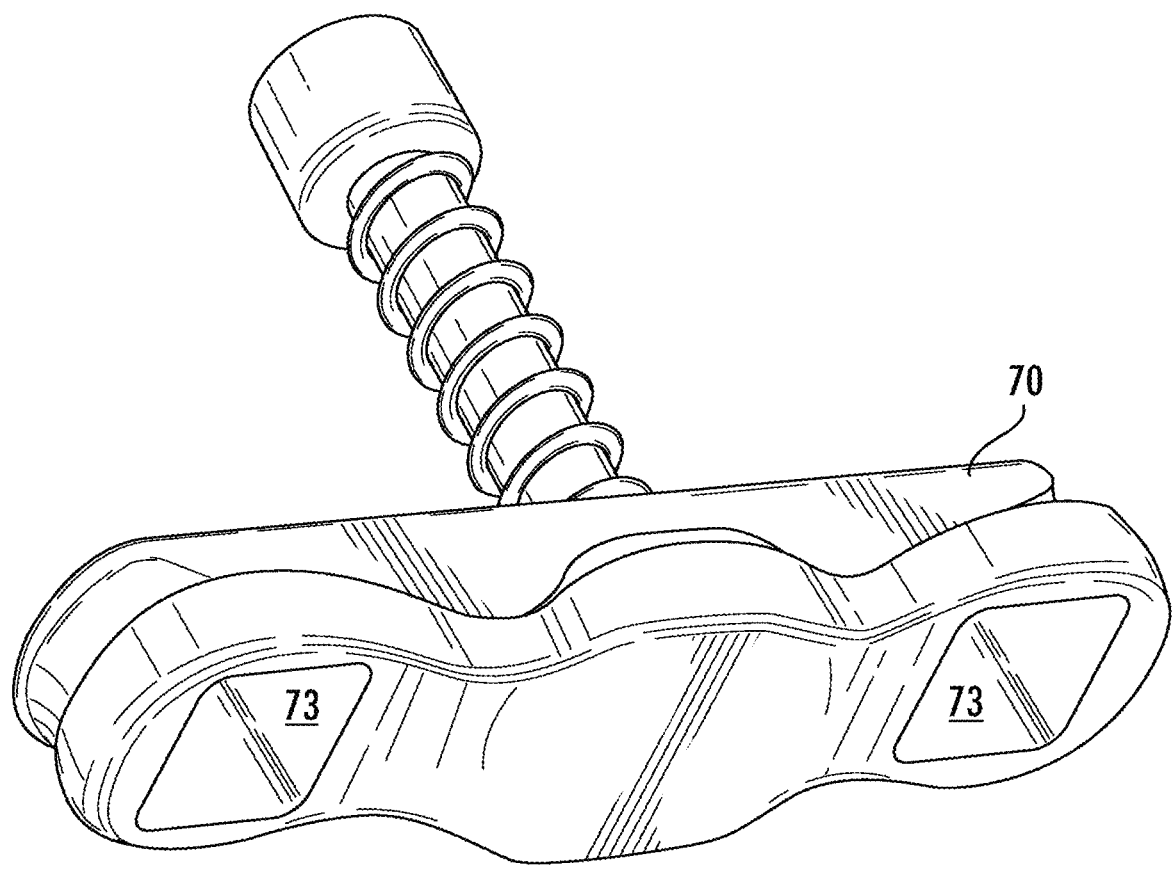
FIG. 13A is a perspective view of the locking mechanism.
Figure 13B:
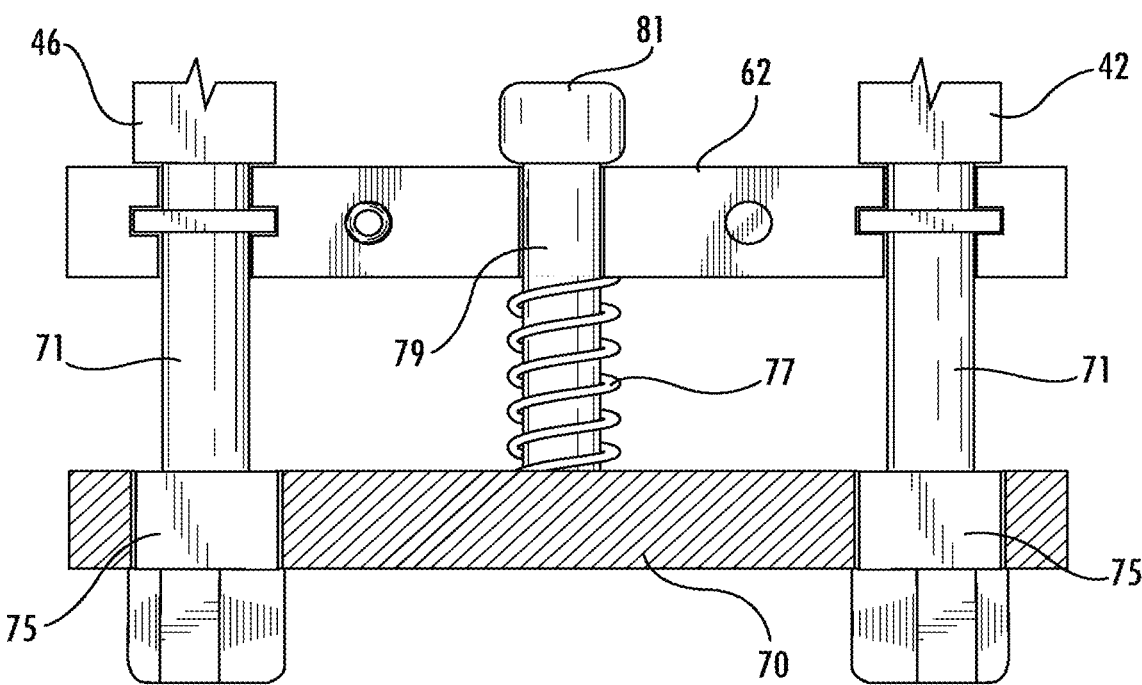
FIG. 13B is a top plan cross sectional view of the drive shafts disengaged by the locking mechanism.
Figure 13C:
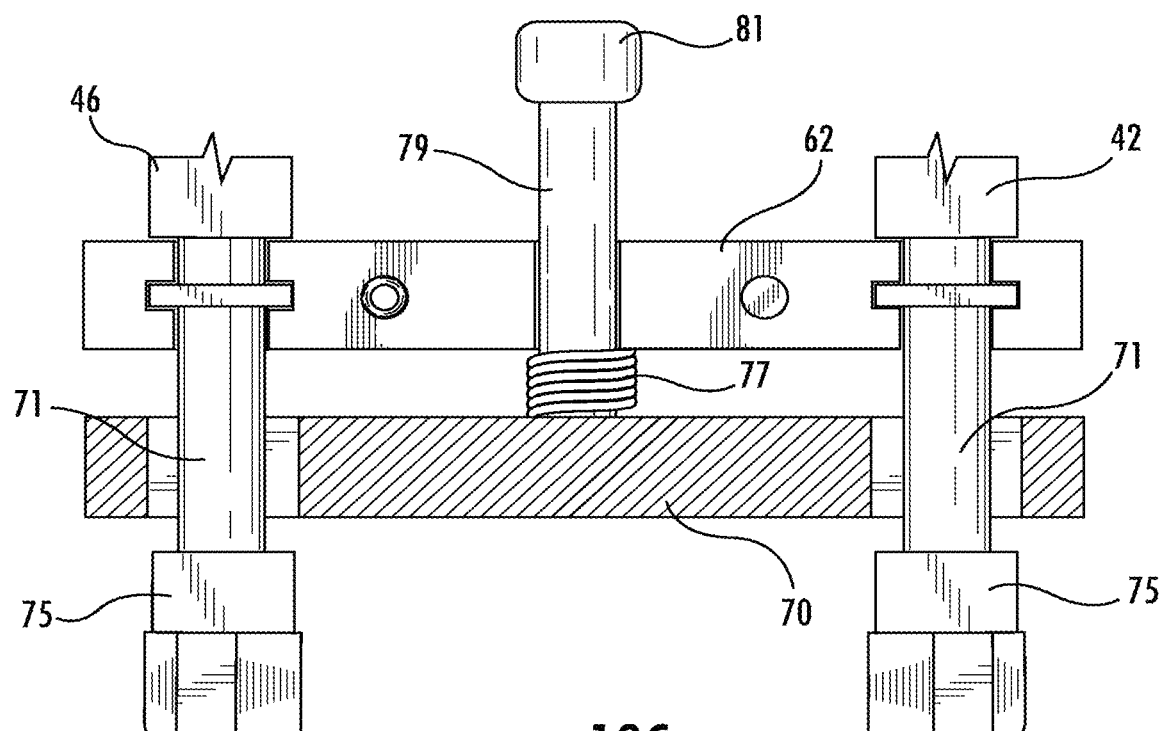
FIG. 13C is a top plan cross sectional view of the drive shafts engaged by the locking mechanism.

A safety lock is provided at the proximal end of the device for preventing unintended rotation of the shafts. As shown in FIGS. 12A and 12B, safety lock member 70 is provided for engagement with the proximal ends of drive shafts 42 and 46. The openings 73 in safety lock member 70 are configured with the shape of the cross-sectional configuration of the drive shafts (see FIG. 13A). A portion of the drive shafts has a narrowed, rounded configuration 71 such that the drive shaft can rotate freely while the rounded portion of the shaft is in alignment with the safety lock member openings 73 (see FIG. 13C). FIG. 12B shows this relationship among the safety lock member 70, thrust bearing 62 and drive shafts 42 and 46. When the non-narrowed portions 75 of the shafts are placed in alignment with the safety lock member openings 73, then rotation of the shafts is prevented (see FIG. 13B). FIG. 12A shows this relationship among the safety lock member 70, thrust bearing 62 and drive shafts 42 and 46. A compression spring 77 can be placed between thrust bearing 62 and safety lock member 70 to urge safety lock member back over the square portion 75 of the drive shafts. FIG. 12B shows a lock disengagement when the safety lock member 70 is pushed forward out of alignment with the square portions 75 and placed in alignment with the rounded portions 71 of shafts 42 and 46. Post 79 can be disposed between safety lock member 70 and thrust bearing 62 on which compression spring 77 can be positioned. Post 79 can be fixedly connected to safety lock member 70 and an opening can be provided in thrust bearing 62 through which post 79 can slide. Post 79 is provided with head 81 to limit the backward movement of safety lock member 70 from the compressive force of spring 77.

The interaction of the tapered external helical threaded members with the step tracking contributes to self-locking under a power screw theory. In considering the variables for promoting a self-locking aspect of the tapered threaded members, certain factors are relevant. In particular, those factors include the coefficient of friction of the materials used, such as Ti-6Al-4V grade 5, the length of pitch of the helical threads and the mean diameter of the tapered member. The following equation explains the relationship among these factors in determining whether the tapered external helical threaded members can self-lock as it travels along the step tracking:

$$T_R = \frac{Fd_m}{2}\left(\frac{l + \pi f d_m \sec\alpha}{\pi d_m - fl \sec\alpha}\right)$$

The above equation determines the torque necessary to apply to the drive shafts engaging the tapered external helical threaded members for expanding the shell members. This torque is dependent upon the mean diameter of the tapered external helical threaded members, the load (F) applied by the adjacent vertebral bodies, the coefficient of friction (f) of the working material, and the lead (l) or, in this embodiment, the pitch of the helical threading. All of these factors determine the required operating torque to transform rotational motion into a linear lift to separate the shell members in accomplishing expansion and lordosis.

The following equation describes the relationship among the factors relating to the torque required to reverse the tapered external helical threaded members back down the tracking:

$$T_R = \frac{Fd_m}{2}\left(\frac{\pi f d_m - l}{\pi d_m + fl}\right)$$

Under this equation, the torque required to lower the tapered external helical threaded members ($T_L$) must be a positive value. When the value of ($T_L$) is zero or positive, self-locking of the tapered external helical threaded members within the step tracking is achieved. If the value of ($T_L$) falls to a negative value, the tapered external helical threaded members are no longer self-locking within the step tracking. The factors that can contribute to a failure to self-lock include the compressive load from the vertebral bodies, the pitch and mean diameter of the helical thread not being adequately great, and an insufficient coefficient of friction of the material. The condition for self-locking is shown below:

$\pi f d_m > l$

Under this condition, it is necessary to select an appropriate combination of sufficient mean diameter size of the tapered member, along with the product material being a greater multiple than the lead or pitch in this particular application so that the tapered members can be self-locking within the step tracking. Based upon average values with a patient lying on their side, the lumbar vertebral body cross sectional area is around 2239 mm² and the axial compressive force at that area is 86.35 N. With the working material selected to be Ti-6Al-4V, the operating torque to expand shell housing 12 between L4-L5 of the vertebral column is around 1.312 lb-in (0.148 N-m), and the operating torque to contract shell housing 12 between L4-L5 of the vertebral column is around 0.264 lb-in (0.029 N-m).

Figure 11A:
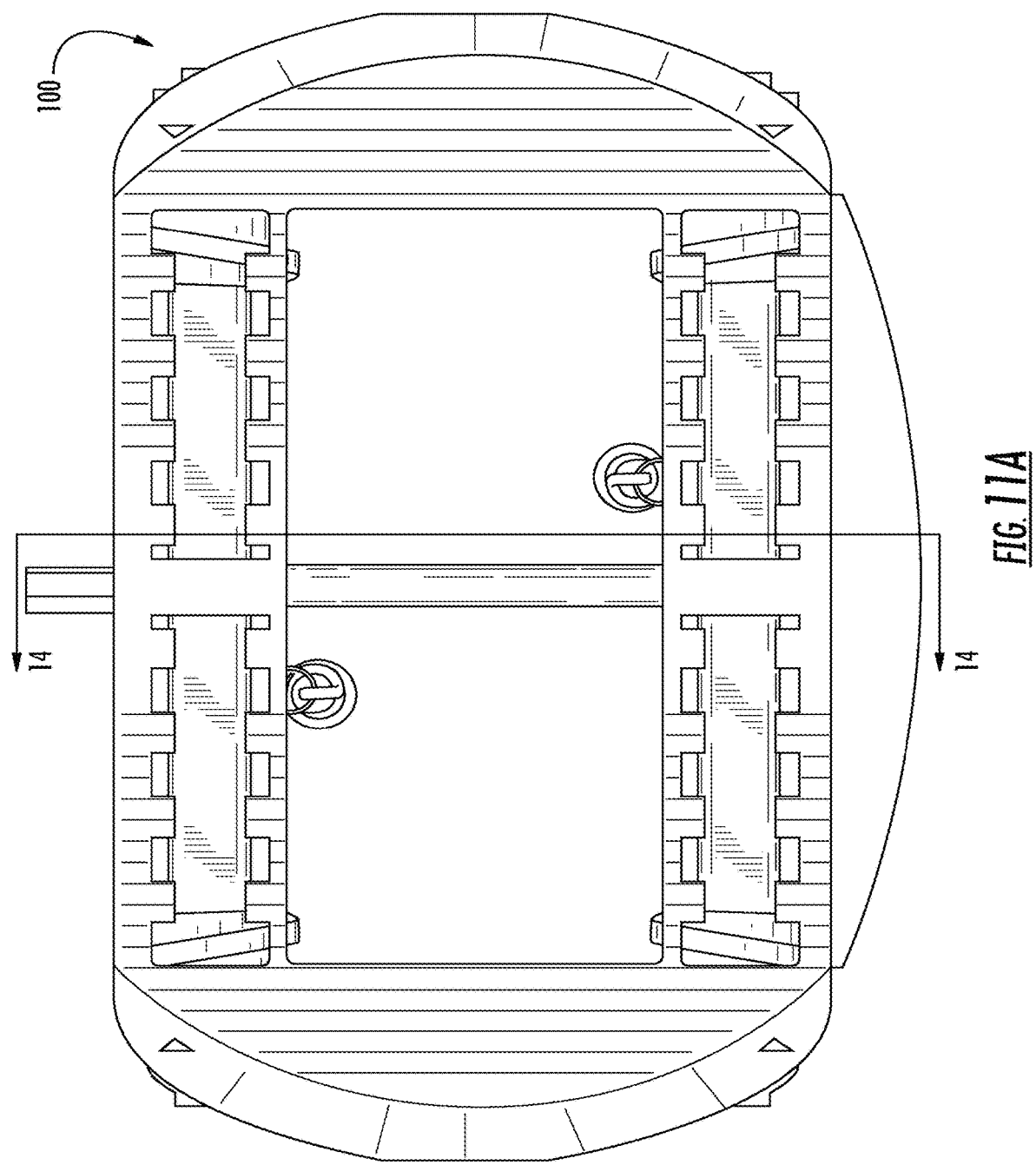
FIG. 11A is a top plan view of another embodiment of the device.

Alternate embodiments of the expandable shell housing provide for different surgical approaches. FIG. 11A shows housing 100 for use where a surgeon approaches the lumbar area from an anterior aspect of the patient. The general configuration of the tracking runs for this embodiment is similar to that for device 10, but the drive shafts for moving the tapered external helical threaded members are applied with a torque delivered from a perpendicular approach. For this, a dual set of worm gears 102 and 104 respectively transfer torque to drive shafts 106 and 108 as shown in FIG. 14.

FIG. 11B shows housing 200 for use where a surgeon approaches the lumbar area from a transforaminal aspect of the patient. The general configuration of the tracking runs for this embodiment is also similar to that for device 10, but the torque is applied to the drive shafts from an offset approach. For this, a dual set of bevel gears (not shown) may be used to transfer torque to drive shafts 206 and 208.

Housing 12 is provided with numerous niches and open areas in its surface and interior regions to accommodate the storage of bone grafting material. The interstitial spaces between the risers of the cascading step tracking also offers areas for receiving bone-grafting material. A membrane can be provided as a supplement around housing 12 to help maintain compression on the top and bottom shells and to hold in bone grafting material. Tension spring elements 78 can be provided to hold together top member 14 and bottom member 16 as shown in FIG. 10. These elements may also serve to provide an initial tension force in the direction opposite of the expansion against the interbody fusion device. This allows the tapered external helical threaded members to climb the risers in the event that contact between the outer shells and the vertebral bodies is not yet made.

Accordingly, this embodiment of the interbody fusion device of the instant invention is capable of expansion to provide support between vertebral bodies and accommodate the load placed on that region. Furthermore, the inventive interbody fusion device is capable of achieving a configuration that can provide an appropriate lordotic tilt to the affected region. The device, therefore, provides a significant improvement with regards to patient-specific disc height adjustment.

The device is provided with a tool for operating the interbody fusion device as it is adjusted in situ in a patient's spine. The operating tool 300 is shown generally in FIG. 16 and comprises a handle member 302, a gear housing 304 and torque rod members 306 and 308. The torque rod members connect to the drive shafts of expandable shell 12. One embodiment for connecting the torque rod members to the drive shafts of expandable shell 12 is shown in FIG. 17. In this arrangement, ends 48 and 50 of drive shafts 42 and 46 can be provided with a hex-shaped head. The ends of torque rod members 306 and 308 can be provided with correspondingly shaped receivers for clamping around ends 48 and 50.

Within the gear housing 304, handle member 302 directly drives torque rod member 308. Torque rod member 308 is provided with spur gear member 310 and torque rod member 306 is provided with spur gear member 312. Spur gear 312 is slidably received on torque rod member 306 and can move in and out of engagement with spur gear 310. Spur gear lever 314 engages with spur gear 312 for moving spur gear 312 into and out of engagement with spur gear 310. When torque rod member 308 is rotated by handle 302, and spur gear 312 is engaged with spur gear 310, rotation is translated to torque rod member 306. In this condition, torque rod member 308 rotates drive shaft 46 simultaneously with torque rod member 306 rotates drive shaft 42 to effect expansion of shell 12 as shown in FIGS. 7A-7C. Spur gear 312 can be moved out of engagement with spur gear 310 by retracting spur gear lever 314 as shown in FIG. 20. With spur gear 312 out of engagement with spur gear 310, rotation of handle 302 only turns torque rod member 308. In this condition, torque rod member 308 rotates drive shaft 46 solely and drive shaft 42 remains inactive to effect the tilt to the top member of shell 12 as shown in FIG. 8 and FIGS. 15A-15C to achieve lordosis.

To achieve expansion of the device in the described embodiment, the operator will turn handle member 302 clockwise to engage torqueing. This applied torque will then engage the compound reverted spur gear train composed of spur gear members 310 and 312. This series of gears will then spin torque rod members 306 and 308 in opposite directions of each other. Torque rod member 308 (in alignment with handle member 302) will spin clockwise (to the right) and torque rod member 306 will spin counterclockwise (to the left). The torque rod members will then rotate the drive shafts of interbody fusion device 12 expanding it to the desired height.

To achieve lordosis the operator will move the spur gear lever 314 back towards handle member 302. By doing so spur gear 312 connected to torque rod member 306 is disengaged from the overall gear train, which in turn will disengage torque rod member 306. As a result, torque rod member 308 will be the only one engaged with the interbody fusion device 12. This will allow the operator to contract the posterior side of the implant device to create the desired degree of lordosis.

Referring now to FIGS. 21-29, various embodiments of a spinal implant device according to the disclosure will now be described.

FIG. 21 is a perspective top view of an exemplary spinal implant device 400 according to embodiments of the disclosure. FIG. 22 is a cross-sectional view of the spinal implant device 400. FIG. 23 is a perspective side view of the spinal implant device 400. FIG. 24 is a cutaway, front view of the spinal implant device 400. As shown in FIGS. 21-24, the exemplary spinal implant device 400 includes an expandable housing 402, a first pair of screw members 404a, 404b, a second pair of screw members 406a, 406b, a first drive shaft 414 engaging with the first pair of screw members 404a, 404b, and a second drive shaft 416 engaging with the second pair of screw members 406a, 406b.

The housing 402 includes a first or bottom shell member 422 and a second or top shell member 424. The bottom shell member 422 may include a plurality of individual riser members 432 (FIG. 23). The top shell member 424 may include a plurality of individual riser members 434 (FIG. 23). The plurality of individual riser members 432, 434 of the bottom and top shell members 422, 424 may define a first step tracking run 436 along a first lateral area 403 of the housing 402 and a second step tracking run 438 along a second lateral area 405 of the housing 402 (FIG. 22). The height of the plurality of individual riser members 432, 434 may change along the first and second step tracking runs 436, 438. For example, the height of the plurality of individual riser members 432, 434 of each of the first and second step tracking runs 436, 438 may increase from a central portion 440 of the step tracking extending distally from the central portion. The first and second pairs of screw members 404a, 404b, 406a, 406b may each comprise an external helical thread having a thickness configured to fit in the gaps between adjacent individual riser members (FIGS. 25-26), to be described in greater detail below.

The first drive shaft 414 is operable to rotate the first pair of screw members 404a, 404b, causing the first pairs of screw members 404a, 404b to move on the individual riser members 432, 434 defining the first step tracking run 436. The second drive shaft 416 is operable to rotate the second pair of screw members 406a, 406b, causing the second pair of screw members 406a, 406b to move on the individual riser members 432, 434 defining the second step tracking run 438. In response to the rotation of the first and second pairs of screw members 404a, 404b, 406a, 406b, the bottom and top shell members 422, 424 may move relative to each other, effecting an expansion of the housing 402 or a contraction of the housing 402 from the expansion by reversing the rotation of the first and/or second pairs of screw members. The first and second drive shafts 414, 416 may be operable independently of each other. Therefore, the degree of expansion or contraction of the first lateral area 403 of the housing 402 is independently adjustable relative to the degree of expansion or contraction of the second lateral area 405 of the housing 402 when the first and second sets of screw members 404a, 404b, 406a, 406b are rotated independently to different positions on the first and second step tracking runs 436, 438.

The positions of the plurality of individual riser members 432 on the bottom shell member 422 may arrange to offset from the positions of the plurality of individual riser members 434 on the top shell member 424 so that the plurality of individual riser members 432 of the bottom shell member 422 may intermesh the plurality of individual riser members 434 of the top shell member 424 when the housing 402 is in a contraction configuration.

The first and second pairs of the screw members 404a, 404b, 406a, 406b may each have a tapered configuration and comprise an external helical thread, as will be described in greater detail below in connection with FIGS. 25-26. The first pair of screw members 404a, 404b may be arranged or disposed such that the directional orientation of the external helical thread of the first screw member 404a of the first pair is opposite to the directional orientation of the second screw member 404b of the first pair so that the first and second screw members 404a, 404b of the first pair move in an opposite direction in the first step tracking run 436 relative to each other upon rotation of the first drive shaft 414. Similarly, the second pair of screw members 406a, 406b may be arranged or disposed such that the directional orientation of the external helical thread of the first screw member 406a of the second pair is opposite to the directional orientation of the external helical thread of the second screw member 406b of the second pair so that the first and second screw members 406a, 406b of the second pair move in an opposite direction in the second step tracking run 438 relative to each other upon rotation of the second drive shaft 416.

By way of example, the first and second pairs of screw members 404a, 404b, 406a, 406b may be arranged such that when the first drive shaft 414 is rotated in a first direction, e.g. clockwise, the first pair of screw members 404a, 404b move distally from the central portion 440 respectively along the first step tracking run 436, and when the second drive shaft 416 is rotated in a second direction opposite to the first direction, e.g. counterclockwise, the second pair of screw members 406a, 406b move distally from the central portion 440 respectively along the second step tracking run 438.

Alternatively, the first and second pairs of screw members 404a, 404b, 406a, 406b may be arranged such that when the first drive shaft 414 is rotated in a first direction the first pair of screw members 404a, 404b move distally from the central portion 440 respectively along the first step tracking run 436, and when the second drive shaft 416 is rotated in a second direction same as the first direction the second pair of screw members 406a, 406b move distally from the central portion 440 respectively along the second step tracking run 438.

Screw Member with Variable Root Radius and Thread Thickness

In some embodiments, the first and second pair of screw members 404a, 404b, 406a, 406b may be tapered screw members having a variable pitch or root radius and an external helical thread with a variable thickness. The variable root radius and thread thickness of the screw members can create a tighter fit between the screw members and the individual risers of the shell members, which in turn reduces, minimizes, or eliminates unwanted micro-motion between parts when the implant device is in its starting position, expanded position or lordotically adjusted position. The variable root radius and thread thickness of the screw members also allow for a more efficient overall operation mechanism when the screw members are moving e.g. climbing up on the individual risers of increasing height. These features allow for a smoother motion and more mechanical efficiency during the expansion, contraction, and lordotic adjustment of the implant device.

FIG. 25 shows an exemplary screw member 450 which can be used as one of the first and second pairs of screw members 404a, 404b, 406a, 406b according to embodiments of the disclosure. As shown, the screw member 450 includes an external helical thread 452 winding from a first end surface 454 to a second end surface 456 of the screw member 450. The screw member 450 may be tapered, e.g., having a root radius at the first end surface 454 different from a root radius at the second end surface 456. As used herein, the term "root radius" refers to a dimension of the screw member 450 measured from the central axis 455 of the screw member 450 perpendicularly to the root surface 458 of the screw member 450.

According to embodiments of the disclosure, the screw member 450 may have a variable root radius at an end surface or at both end surfaces of the screw member 450. As shown in FIG. 25, at the first end surface 454 the screw member 450 may have a first root radius $R_1$ and a second root radius $R_2$ where $R_1$ and $R_2$ differ, e.g. $R_1$ is greater than $R_2$ as shown. At the second end surface 456, the screw member 450 may have a first root radius $r_1$ and a second root radius $r_2$ where $r_1$ and $r_2$ differ, e.g. $r_1$ is less than $r_2$ as shown. In some embodiments, a root radius of the screw member 450 may be ever-changing or change continuously from the first end surface 454 to the second end surface 456. For example, as shown in FIG. 25, the change of the root radius from $R_1$ to $r_1$ may be continuous from the first end surface 454 to the second end surface 456 of the screw member 450, or the change of the root radius from $R_2$ to $r_2$ may be continuous from the first end surface 454 to the second end surface 456 of the screw member 450. Variable root radius allows the screw member 450 to sit on two individual risers of different heights simultaneously.

According to embodiments of the disclosure, the external thread 452 of the screw member 450 may have a variable thickness. As shown in FIG. 25, the external thread 452 may have a first thickness $T_1$ at the first end surface 454 and a second thickness $T_2$ at the second end surface 456 where $T_1$ and $T_2$ differ, e.g., $T_1$ is greater than $T_2$ as shown. According to embodiments of the disclosure, the thickness of at least a portion of the thread 452 is ever-changing, or changes continuously or constantly. In some preferred embodiments, the thickness of the entire external thread 452 may continuously change from the first end surface 454 to the second end surface 456.

Referring to FIG. 26, according to embodiments of the disclosure, the side surfaces of the thread of the screw member 450 may be angled. For example, as indicated by line 464 in FIG. 26, the side surface 460 of the thread of the screw member 450 may be angled, i.e., non-perpendicular to the root surface 458 of the screw member 450. According to embodiments of the disclosure, a portion of the side surfaces of the riser members may also be angled. For example, as indicated by line 466 in FIG. 26, a portion of the side surface of the riser member 434 may be angled or chamfered, i.e., non-perpendicular to the end surfaces of the riser 434. As shown in FIG. 26, at least a portion of the side surface 462 of the riser 432 is angled. The angled side surfaces of the screw members and/or riser members can make the contact between the screw members and the riser members at different points simultaneously, allowing for a smooth motion of the screw members along the step track runs as torque is applied to the drive shafts causing the screw members to rotate and travel.

The features of the screw member 450 provided by this disclosure create a tighter fit of the screw member in the gaps of individual risers. The tighter fit between the screw member and the individual risers allows the implant device to keep stabilized once implanted in between the patient's intervertebral bodies of the spine and eliminate or reduce unwanted micro-motion. This will help to keep the patient's vertebral space fixed to the position where the doctor set and promote bone fusion in a better manner. The tighter fit between the screw member and the individual risers also allows for a smooth operation during surgery while the surgeon is using a surgical instrument such as an inserter tool to expand and/or lordotically adjust the implant once implant device is placed in-between the patient's vertebral bodies. It also allows for a fluid and strong distraction force during surgery. In cases where the patient's vertebral disc space is collapsed, the mechanism can be used to distract the disc space to restore the correct intervertebral disc height.

Extension Springs

In some embodiments, an exemplary spinal implant device according to this disclosure may include one or more extension springs to assure that the entire implant device stays together. Extreme coronal or sagittal imbalances may exist in patients, which may apply uneven distribution of forces on the implant device when implanted in the patients. Uneven distribution of forces on the internal mechanism may cause disassociation of the device. Even before being implanted in the patient, the device may drop, experience vibration or rattling, causing the device to disassociate.

The extension spring(s) provided in the implant device of the disclosure can keep the top and bottom shell members together during its fully contracted state so that in case the device is dropped, experiences vibration or rattling, all components in the device are still held together.

The extension spring may also work to keep an opposing force on the assembly. The mechanism inside the device may undergo expansion and/or lordotic adjustment once pressure is applied to the top and bottom shell members of the device. An equal and opposite force may be needed for the mechanism to move efficiently and correctly. The extension springs provided in the device of this disclosure may create an initial tension against the mechanism, allowing it to expand and/or adjust lordotically when, for example, the patient's vertebral bodies have not made contact with the device.

The extension springs may also work to keep the end surfaces or tips of the individual risers against the root surface and threads of the screw members once expansion and/or lordotic adjustment has taken place. This assures that the whole assembly of the device stays together in its expanded or lordotically adjusted positions.

Referring now to FIGS. 21-24, the implant device 400 may include a first extension spring 472 coupling the bottom and top shell members 422, 424 and a second extension spring 474 coupling the bottom and top shell members 422, 424. It should be noted that one or more than two extension springs may be provided in the implant device and adequately perform the functions. The first extension spring 472 may be coupled to the top and bottom sell members adjacent to the first step tracking run. The second extension spring 474 may be coupled to the top and bottom shell members adjacent to the second step tracking run. The extension springs 472, 474 may be attached to the top and bottom shell members using any suitable means. By way of example, the extension springs 472, 474 may have hooks at both ends of the springs that hook into loops in the bottom and top shell members 422, 424 as shown. The extension springs 472, 474 may also be welded to the top and bottom shell members at the ends of the hooks.

In surgical cases where the implant device is inserted into a patient having a large intervertebral disc space anatomy, the extension springs 472, 474 can provide an opposing force down on the internal mechanism of the implant device 400 to allow it to expand or lordotically adjust until it has contacted the patient's vertebral bodies. In surgical cases where the implant device 400 is inserted into a patient having a high level of lordotic, kyphotic, or coronal imbalances, the extension springs 472, 474 will work to apply an opposing force through tension to keep the mechanism of the implant in contact with itself. This will allow the doctor to place the implant in between these imbalanced disc spaces and allow the surgeon to help correct the disc spaces back to a normal sagittal and coronal balance.

Bearing Snap Fit and Graft Ramp

Returning to FIGS. 21-24, in some preferred embodiments, the spinal implant device 400 may include at least one thrust bearing 480 configured to limit axial and/or lateral movement of the drive shafts 414, 416 while allowing the drive shafts to rotate or spin about the longitudinal axes of the drive shafts. The thrust bearing 480 may be designed to have a ramp-like geometry 486 that allows an instrument carrying a bone graft material to be guided into the implant housing 402. This device feature allows for a more efficient surgical instrument interface with the implant device, ultimately making the surgery more efficient.

FIG. 27 is an exploded view of an exemplary thrust bearing 480 according to embodiments of the disclosure. As shown, the thrust bearing 480 may have a yoke-like configuration comprising a first or top part 482 and a second or bottom part 484. When connected, the top and bottom parts 482, 484 of the thrust bearing 480 define a pair of openings or bearing sites for receiving or locking the pair of drive shafts 414, 416 e.g. at the end portions of the drive shafts.

The top and bottom parts 482, 484 of the thrust bearing 480 may be connected by snap-fit or press-fit through features provided on the top and bottom parts respectively. For example, as shown in FIGS. 27-29, the bottom part 484 of the thrust bearing 480 may include protrusions or guides 486 shaped and sized to be received in corresponding recesses 488 in the top part 482 of the bearing 480 by interference fit. In some preferred embodiments, the snap-fit features in the top and bottom parts 482, 484 of the bearing 480 may be configured such that when the top and bottom parts 482, 484 are connected, a portion of the bottom part 484 overlaps with a portion of the top part 482, allowing the top and bottom parts 482, 484 to be more "hooked" or connected, as better shown in FIG. 24.

Referring to FIG. 29, the drive shafts 414, 416 may each have a rounded portion 415 of a diameter less than the squared or remaining portion of the drive shaft. The top and bottom parts 482, 484 of the thrust bearing 480 may be configured or sized such that when the top and bottom parts 482, 484 are connected, the rounded portions 415 of the drive shafts 414, 416 are received in the openings or bearing sites of thrust bearing 480, thereby preventing the drive shafts 414, 416 from moving axially or laterally while allowing the drive shafts 414, 416 to spin or rotate about their longitudinal axes. In some embodiments, the drive shafts 414, 416 may each be provided with an annular ridge 417 in the rounded portion 415. The top and bottom parts 482, 484 of the thrust bearing 480 may each be provided with a groove 483, 485 (better shown in FIGS. 27 and 28) so that when the top and bottom parts 482, 484 are connected a journal of the bearing is formed. The annular ridge 417 on the drive shaft may be received in the grooves 483, 485 of the bearing 480, providing an improved engagement of the draft shaft with the thrust bearing. The implant device 400 may include at least one or preferably two thrust bearings 480 at an end portion or both end portions of the drive shafts.

Still referring to FIGS. 27-29, the top part 482 of the bearing 480 may include a "ramp-like" geometry or flat section 486 between the two curved end sections. This ramp-like section 486, in conjunction with the top shell 424 of the housing 402, provides an easy access for a surgical instrument carrying a bone graft material to be guided into the housing of the implant device 400, as better shown in FIG. 21.

Still referring to FIGS. 27-29, in some embodiments, the thrust bearing 480 may be configured to accommodate certain variance of the drive shafts 414, 416 in the operation of the implant device 400. For example, when the implant device 400 is in a parallel configuration as shown in FIG. 30, the drive shafts 414, 416 are closer. When the implant device 40 is in a lordosis configuration as shown in FIG. 31, the drive shafts 414, 416 are farther apart from each other. The bearing openings may be configured to be "slotted" rather than being perfectly circular to accommodate the variance, as shown in FIGS. 30-31.

Various embodiments of an expandable and adjustable Lordosis interbody fusion device have been described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise.

Those skilled in the art will appreciate that various other modifications may be made. All these or other variations and modifications are contemplated by the inventors and within the scope of the invention.

The invention claimed is:

1. A device for placement between vertebral bodies, the device comprising:
a housing;
at least one screw member in the housing; and
at least one drive shaft operably engageable with the at least one screw member, wherein
the housing comprises a first shell member and a second shell member, at least the first shell member having step tracking comprising a plurality of individual riser members for receiving the at least one screw member, the plurality of individual riser members extending a height from an inner surface of the first shell member, the height of the plurality of individual riser members changing along the step tracking,
the drive shaft is operable to rotate the at least one screw member causing the at least one screw member to move on the plurality of individual riser members, and
the at least one screw member comprises an external helical thread having a thickness configured to fit in a gap between adjacent individual riser members, and a root surface engageable with the plurality of individual riser members wherein when the root surface of the at least one screw member is in contact with at least one of the plurality of individual riser members, a peak of the external helical thread of the at least one screw member is spaced from the inner surface of the first shell member, and the first and second shell members move relative to each other in response to rotation of the at least one screw member to effect an expansion of the housing or a contraction of the housing from the expansion by reversing the rotation of the at least one screw member.

2. The device of claim 1, wherein at least a portion of the external helical thread has a continuously changing thickness.

3. The device of claim 1, wherein the plurality of individual riser members have angled side surfaces configured to engage with the external helical thread.

4. The device of claim 1, wherein the at least one screw member comprises a variable root radius.

5. The device of claim 4, wherein the at least one screw member is tapered from a first end surface to a second end surface and comprises a continuously changing root radius from the first end surface to the second end surface of the at least one screw member.

6. The device of claim 5, wherein the external helical thread of the at least one screw member has a continuously changing thickness from the first end surface to the second end surface.

7. The device of claim 6, further comprising at least one extension spring coupled to the first and the second shell members holding the first and second shell members together at a starting height and/or during expansion and/or contraction of the housing.

8. The device of claim 1, further comprising at least one extension spring coupled to the first and the second shell members holding the first and second shell members together at a starting height and/or during expansion and/or contraction of the housing.

9. The device of claim 1, wherein the plurality of individual riser members are arranged successively along the step tracking in two series forming a travel pathway for the at least one screw member, wherein riser members in one of the two series are spaced apart from riser members in another one of the two series.

10. A device for placement between vertebral bodies, the device comprising:
a housing;
a first set of screw members and a second set of screw members in the housing;
a first drive shaft operably engageable with the first set of screw members and a second drive shaft operably engageable with the second set of screw members, wherein
the housing comprises a first shell member and a second shell member each having a plurality of individual riser members, the plurality of individual riser members of the first and second shell members extending a height from an inner surface of the first and second shell members respectively, wherein the plurality of individual riser members of the first and second shell members defining a first step tracking run along a first lateral area of the housing and a second step tracking run along a second lateral area of the housing, the height of the plurality of individual riser members changing along the first and second step tracking runs,
the first drive shaft is operable to rotate the first set of screw members causing the first set of screw members to move along the first step tracking run, the second drive shaft is operable to rotate the second set of screw members causing the second set of screw members to move along the second step tracking run, the first and second drive shafts being operable independently of each other,
the first and second sets of screw members each comprises an external helical thread having a thickness configured to fit in a gap between adjacent individual riser members, and a root surface engageable with the plurality of individual riser members of the first and second shell members respectively, wherein when the root surface of at least one of the first and second sets of screw members is in contact with at least one of the plurality of individual riser members of the first and second shell members, a peak of the external helical thread of the at least one of the first and second sets of screw members is spaced from the inner surface of the first or second shell member, and the first and second shell members move relative to each other in response to rotation of the first and/or second sets of screw members to effect an expansion of the housing or a contraction of the housing from the expansion by reversing the rotation of the first and/or second sets of screw members, wherein a degree of expansion or contraction of the first lateral area of the housing is independently adjustable relative to a degree of expansion or contraction of the second lateral area of the housing when the first and second sets of screw members are rotated independently to different positions on the first and second step tracking runs.

11. The device of claim 10, wherein the external helical thread of each of the first and second sets of screw members has a continuously changing thickness.

12. The device of claim 10, wherein the plurality of individual riser members have an angled side surfaces configured to engage with the external helical thread of each of the first and second sets of screw members.

13. The device of claim 10, wherein each of the first and second sets of screw members comprises a variable root radius.

14. The device of claim 10, wherein each of the first and second sets of screw members is tapered from a first end surface to a second end surface and comprises a continuously changing root radius from the first end surface to the second end surface.

15. The device of claim 14, wherein the external helical thread of each of the first and second sets of screw members has a continuously changing thickness from the first end surface to the second end surface.

16. The device of claim 15, further comprising at least one extension spring coupled to the first and the second shell members holding the first and second shell members together at a starting height and/or during adjustment and/or during expansion and/or contraction of the housing.

17. The device of claim 10, further comprising at least one extension spring coupled to the first and the second shell members holding the first and second shell members together at a starting height and/or during lordosis adjustment and/or during expansion and/or contraction of the housing.

18. The device of claim 10, further comprising at least one thrust bearing configured to prevent axial and/or lateral movement of the first and second drive shafts, wherein the thrust bearing comprises a first part and a second part configured to snap fit together providing a first bearing site engaging the first drive shaft and a second bearing site engaging the second drive shaft.

19. The device of claim 18, wherein the second part of the thrust bearing member comprises a middle section between the first and second bearing sites, wherein the middle section has a ramp geometry allowing an instrument carrying a graft material to be guided into the housing.

20. The device of claim 18, wherein the first and second bearing sites of the at least one thrust bearing are configured to provide openings that are slotted to accommodate variance in space between the first and second drive shafts depending on the degree of independent adjustment made to the first lateral area relative to the second lateral area.

21. The device of claim 10, wherein the plurality of individual riser members of the first and second shell members are arranged successively along the first and second step tracking runs respectively in two series respectively, forming a first travel pathway for the first set of screw members and a second travel pathway for the second set of screw members respectively, wherein riser members in one of the two series of the first travel pathway are spaced apart from riser members in another one of the two series of the first travel pathway, and riser members in one of the two series of the second travel pathway are spaced apart from riser members in another one of the two series of the second travel pathway.

* * * * *